(12) United States Patent
Hungenberg et al.

(10) Patent No.: US 8,828,907 B2
(45) Date of Patent: Sep. 9, 2014

(54) ACTIVE INGREDIENT COMBINATIONS HAVING INSECTICIDAL AND ACARICIDAL PROPERTIES

(75) Inventors: Heike Hungenberg, Langenfeld (DE); Peter Jeschke, Bergisch Gladbach (DE); Robert Velten, Langenfeld (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 232 days.

(21) Appl. No.: 13/259,937

(22) PCT Filed: Mar. 25, 2009

(86) PCT No.: PCT/EP2009/002169
§ 371 (c)(1),
(2), (4) Date: Dec. 12, 2011

(87) PCT Pub. No.: WO2010/108506
PCT Pub. Date: Sep. 30, 2010

(65) Prior Publication Data
US 2012/0077675 A1    Mar. 29, 2012

(51) Int. Cl.
*A01N 33/26* (2006.01)
*A01N 37/40* (2006.01)
*A01N 43/40* (2006.01)
*A01P 7/04* (2006.01)

(52) U.S. Cl.
CPC .................... *A01N 43/40* (2013.01)
USPC .................. 504/100; 514/336; 514/615

(58) Field of Classification Search
USPC .................. 514/336, 365, 615; 504/100
See application file for complete search history.

(56) References Cited

U.S. PATENT DOCUMENTS

| | | |
|---|---|---|
| 3,748,356 A | 7/1973 | Wellinga et al. |
| 4,097,581 A | 6/1978 | Farooq et al. |
| 4,139,636 A | 2/1979 | Sirrenberg et al. |
| 4,215,139 A | 7/1980 | Fischer et al. |
| 4,245,432 A | 1/1981 | Dannelly |
| 4,272,417 A | 6/1981 | Barke et al. |
| 4,457,943 A | 7/1984 | Becher et al. |
| 4,550,202 A | 10/1985 | Brouwer et al. |
| 4,623,658 A | 11/1986 | Anderson |
| 4,677,127 A | 6/1987 | Böger |
| 4,761,373 A | 8/1988 | Anderson et al. |
| 4,798,837 A | 1/1989 | Drabek et al. |
| 4,808,430 A | 2/1989 | Kouno |
| 4,980,376 A | 12/1990 | Massardo et al. |
| 4,985,461 A | 1/1991 | Hsu et al. |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,344,958 A | 9/1994 | Lidert et al. |
| 5,378,726 A | 1/1995 | Yanagi et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,789,566 A | 8/1998 | Bonhomme et al. |
| 5,824,790 A | 10/1998 | Keeling et al. |
| 5,840,946 A | 11/1998 | Wong et al. |

(Continued)

FOREIGN PATENT DOCUMENTS

| CA | 1079285 A | 6/1980 |
|---|---|---|
| CN | 1313276 A | 9/2001 |

(Continued)

OTHER PUBLICATIONS

Hackh's Chemical Dictionary, 4$^{th}$ ed., McGraw-Hill Book Co., New York, p. 170 (1977).*

(Continued)

*Primary Examiner* — John Pak
(74) *Attorney, Agent, or Firm* — Sterne, Kessler, Goldstein & Fox P.L.L.C.

(57) ABSTRACT

The present invention relates to novel active compound combinations comprising, firstly, at least one known compound of the formula (I)

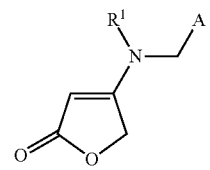

(I)

in which
R$^1$ and A have the meanings given in the description
and, secondly, at least one further known active compound from the class of the chitin synthesis inhibitors, the molting hormone agonists or other classes, which combinations are highly suitable for controlling animal pests such as insects and unwanted acarids.

11 Claims, No Drawings

(56) References Cited

U.S. PATENT DOCUMENTS

| | | |
|---|---|---|
| 5,866,782 A | 2/1999 | Iwabuchi et al. |
| 5,876,739 A | 3/1999 | Turnblad et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |
| 5,969,169 A | 10/1999 | Fan |
| 6,001,628 A | 12/1999 | Kossmann et al. |
| 6,013,861 A | 1/2000 | Bird et al. |
| 6,063,947 A | 5/2000 | DeBonte et al. |
| 6,162,966 A | 12/2000 | Kossmann et al. |
| 6,169,190 B1 | 1/2001 | Lanuza et al. |
| 6,229,072 B1 | 5/2001 | Burns et al. |
| 6,245,968 B1 | 6/2001 | Boudec et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,323,392 B1 | 11/2001 | Charne |
| 6,566,587 B1 | 5/2003 | Lebrun et al. |
| 6,590,141 B1 | 7/2003 | Frohberg |
| 6,734,341 B2 | 5/2004 | Singletary et al. |
| 6,791,010 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 7,112,665 B1 | 9/2006 | Leemans et al. |
| 7,186,898 B1 | 3/2007 | Kossmann et al. |
| 7,304,209 B2 | 12/2007 | Zink et al. |
| 2001/0007155 A1 | 7/2001 | Kossmann et al. |
| 2001/0011378 A1 | 8/2001 | Kossmann et al. |
| 2002/0008823 A1 | 1/2002 | Murayama et al. |
| 2002/0031826 A1 | 3/2002 | Nichols |
| 2002/0092040 A1 | 7/2002 | Kossmann et al. |
| 2002/0133849 A1 | 9/2002 | Kossmann et al. |
| 2002/0138876 A1 | 9/2002 | Block et al. |
| 2002/0162138 A1 | 10/2002 | Kossmann et al. |
| 2003/0093834 A1 | 5/2003 | Loerz et al. |
| 2003/0106100 A1 | 6/2003 | Kossmann et al. |
| 2003/0138927 A1 | 7/2003 | Heyer et al. |
| 2003/0167527 A1 | 9/2003 | Emmermann et al. |
| 2003/0167529 A1 | 9/2003 | Landschutze |
| 2003/0176428 A1 | 9/2003 | Schneidersmann et al. |
| 2003/0229923 A1 | 12/2003 | Kossmann et al. |
| 2004/0014092 A1 | 1/2004 | Heyer et al. |
| 2004/0110254 A1 | 6/2004 | Buttcher et al. |
| 2005/0257283 A1 | 11/2005 | Matringe et al. |
| 2006/0015966 A1 | 1/2006 | Landschutze |
| 2006/0168690 A1 | 7/2006 | Shibatani et al. |
| 2008/0250533 A1 | 10/2008 | Frohberg |
| 2009/0247551 A1 | 10/2009 | Jeschke et al. |
| 2009/0253749 A1 | 10/2009 | Jeschke et al. |
| 2010/0240705 A1 | 9/2010 | Jeschke et al. |
| 2012/0021901 A1 | 1/2012 | Hungenberg et al. |
| 2012/0035050 A1 | 2/2012 | Jeschke et al. |
| 2012/0094829 A1 | 4/2012 | Jeschke et al. |
| 2012/0115720 A1 | 5/2012 | Hungenberg et al. |

FOREIGN PATENT DOCUMENTS

| | | | |
|---|---|---|---|
| EP | 0 071 279 A1 | 2/1983 | |
| EP | 0 228 564 A2 | 7/1987 | |
| EP | 0 539 588 A1 | 5/1993 | |
| EP | 0 719 338 B1 | 7/1996 | |
| EP | 0 728 213 B1 | 8/1996 | |
| EP | 0 571 427 B1 | 10/2003 | |
| EP | 0 663 956 B1 | 7/2005 | |
| GB | 1 587 573 | 4/1981 | |
| GB | 2 140 010 A | 11/1984 | |
| JP | 2006-304779 A | 11/2006 | |
| WO | WO 89/10396 A1 | 11/1989 | |
| WO | WO 91/02069 A1 | 2/1991 | |
| WO | WO 94/04693 A2 | 3/1994 | |
| WO | WO 94/09144 A1 | 4/1994 | |
| WO | WO 94/11520 A2 | 5/1994 | |
| WO | WO 94/21795 A1 | 9/1994 | |
| WO | WO 95/26407 A1 | 10/1995 | |
| WO | WO 95/35026 B2 | 12/1995 | |
| WO | WO 96/01904 A1 | 1/1996 | |
| WO | WO 96/19581 A1 | 6/1996 | |
| WO | WO 96/21023 A1 | 7/1996 | |
| WO | WO 96/33270 A1 | 10/1996 | |
| WO | WO 96/34968 A2 | 11/1996 | |
| WO | WO 97/20936 A1 | 6/1997 | |
| WO | WO 97/41218 A1 | 11/1997 | |
| WO | WO 97/47806 A1 | 12/1997 | |
| WO | WO 97/47807 A1 | 12/1997 | |
| WO | WO 97/47808 A1 | 12/1997 | |
| WO | WO 98/00394 A1 | 1/1998 | |
| WO | WO 98/00549 A1 | 1/1998 | |
| WO | WO 98/19542 A1 | 5/1998 | |
| WO | WO 98/20145 A2 | 5/1998 | |
| WO | WO 98/22604 A1 | 5/1998 | |
| WO | WO 98/27806 A1 | 7/1998 | |
| WO | WO 98/32326 A2 | 7/1998 | |
| WO | WO 99/12950 A2 | 3/1999 | |
| WO | WO 99/53072 A1 | 10/1999 | |
| WO | WO 99/57965 A1 | 11/1999 | |
| WO | WO 99/66050 A1 | 12/1999 | |
| WO | WO 00/04173 A1 | 1/2000 | |
| WO | WO 00/11192 A2 | 3/2000 | |
| WO | WO 00/14249 A1 | 3/2000 | |
| WO | WO 00/28052 A2 | 5/2000 | |
| WO | WO 00/66746 A1 | 11/2000 | |
| WO | WO 00/66747 A1 | 11/2000 | |
| WO | WO 00/73422 A1 | 12/2000 | |
| WO | WO 00/77229 A2 | 12/2000 | |
| WO | WO 01/14569 A2 | 3/2001 | |
| WO | WO 01/17333 A1 | 3/2001 | |
| WO | WO 01/19975 A2 | 3/2001 | |
| WO | WO 01/24615 A1 | 4/2001 | |
| WO | WO 01/65922 A2 | 9/2001 | |
| WO | WO 01/66704 A2 | 9/2001 | |
| WO | WO 01/98509 A2 | 12/2001 | |
| WO | WO 02/26995 A1 | 4/2002 | |
| WO | WO 02/28186 A2 | 4/2002 | |
| WO | WO 02/34923 A2 | 5/2002 | |
| WO | WO 02/36782 A2 | 5/2002 | |
| WO | WO 02/45485 A1 | 6/2002 | |
| WO | WO 02/079410 A2 | 10/2002 | |
| WO | WO 02/080675 A1 | 10/2002 | |
| WO | WO 02/101059 A2 | 12/2002 | |
| WO | WO 03/013226 A2 | 2/2003 | |
| WO | WO 03/033540 A1 | 4/2003 | |
| WO | WO 03/071860 A2 | 9/2003 | |
| WO | WO 03/092360 A2 | 11/2003 | |
| WO | WO 2004/040012 A2 | 5/2004 | |
| WO | WO 2004/053219 A2 | 6/2004 | |
| WO | WO 2004/056999 A1 | 7/2004 | |
| WO | WO 2004/078983 A2 | 9/2004 | |
| WO | WO 2004/090140 A2 | 10/2004 | |
| WO | WO 2004/106529 A2 | 12/2004 | |
| WO | WO 2005/002324 A2 | 1/2005 | |
| WO | WO 2005/002359 A2 | 1/2005 | |
| WO | WO 2005/012515 A2 | 2/2005 | |
| WO | WO 2005/017157 A1 | 2/2005 | |
| WO | WO 2005/020673 A1 | 3/2005 | |
| WO | WO 2005/030941 A1 | 4/2005 | |
| WO | WO 2005/030942 A1 | 4/2005 | |
| WO | WO 2005/093093 A2 | 10/2005 | |
| WO | WO 2005/095617 A2 | 10/2005 | |
| WO | WO 2005/095618 A2 | 10/2005 | |
| WO | WO 2005/095619 A1 | 10/2005 | |
| WO | WO 2005/095632 A2 | 10/2005 | |
| WO | WO 2005/123927 A1 | 12/2005 | |
| WO | WO 2006/007373 A2 | 1/2006 | |
| WO | WO 2006/015376 A2 | 2/2006 | |
| WO | WO 2006/018319 A1 | 2/2006 | |
| WO | WO 2006/021972 A1 | 3/2006 | |
| WO | WO 2006/024351 A1 | 3/2006 | |
| WO | WO 2006/032469 A2 | 3/2006 | |
| WO | WO 2006/032538 A1 | 3/2006 | |
| WO | WO 2006/045633 A1 | 5/2006 | |
| WO | WO 2006/060634 A2 | 6/2006 | |

(56) References Cited

FOREIGN PATENT DOCUMENTS

| WO | WO 2006/063862 A1 | 6/2006 |
|---|---|---|
| WO | WO 2006/072603 A2 | 7/2006 |
| WO | WO 2006/103107 A1 | 10/2006 |
| WO | WO 2006/108702 A1 | 10/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO2007/107326 A1 | 9/2007 |
| WO | WO 2007/112843 A1 | 10/2007 |
| WO | WO 2007/115643 A1 | 10/2007 |
| WO | WO 2007/115644 A1 | 10/2007 |
| WO | WO 2007/131699 A2 | 11/2007 |
| WO | WO 2008/017518 A1 | 2/2008 |
| WO | WO 2008/080630 A1 | 7/2008 |
| WO | WO 2008/080631 A1 | 7/2008 |
| WO | WO 2008/090008 A1 | 7/2008 |

OTHER PUBLICATIONS

HCAPLUS abstract 1997:60236 (1997).*
HCAPLUS abstract 1997:503825 (1997).*
HCAPLUS abstract 1997:161121 (1997).*
Barry, G., et al., "Inhibitors of Amino Acid Biosynthesis: Strategies for Imparting Glyphosate Tolerance to Crop Plants," *Curr. Topics Plant Physiol.* 7:139-145, American Society of Plant Physiologists, United States (1992).
Colby, S.R., "Calculating Synergistic and Antagonistic Responses of Herbicide Combinations," *Weeds 15*:20-22, Weed Science Society of America, United States (1967).
Comai, L., et al., "An Altered aroA Gene Product Confers Resistance to the Herbicide Glyphosate," *Science 221*:370-371, American Association for the Advancement of Science, United States (1983).
Crickmore, N., "The VIP Nomenclature," as referenced in *Bacillus thurigiensis* Toxin Nomenclature, main page accessed on Feb. 3, 2012 at <lifesci.sussex.ac.uk/home/Neil_Crickmore/Bt/intro.html>, and the link to the nomenclature accessed at <lifesci.sussex.ac.uk/home/Neil_Crickmore/Bt/vip.html>.
Crickmore, N., et al., "Revision of the Nomenclature for the *Bacillus thuringiensis* Pesticidal Crystal Proteins," *Microbiol. Mol. Biol. Rev.* 62(3):807-813, American Society for Microbiology, United States (1998).
"Deliberate releases and placing on the EU market of Genetically Modified Organisms—GMO Register," European Commission, Joint Research Centre, Institute for Health and Consumer Protection, accessed on Feb. 3, 2012 at <gmoinfo.jrc.ec.europa.eu/gmp_browse.aspx> 38 pages.
Draber W., "Chemie der Pflanzenschutz-und Schadlingsbekampfungsmittel [Chemistry of Plant Protection and Pest Control Agents]," R. Wegler (eds.) 2:400-412, Springer-Verlag, Berlin (1970).
English language translation of Draber W., "Chemie der Pflanzenschutz-und Schadlingsbekampfungsmittel [Chemistry of Plant Protection and Pest Control Agents]," R. Wegler (eds.) 2:400-412, Springer-Verlag, Berlin (1970).
Gasser, C.S., et al., "Structure, Expression, and Evolution of the 5-Enolpyruvylshikimate- 3-phosphate Synthase Genes of Petunia and Tomato," *J. Biol. Chem.* 263(9):4280-4289, The American Society for Biochemistry and Molecular Biology, Inc., United States (1988).
Kanno, H. and Ikeda, K., "2-tert-Butylimino-3-Isopropyl-5-Phenylperhydro-1,3,5-Thiadiazin-4-One (NNI-750), A New Insecticide," *Proceedings 1981 British Crop Protection Conference—Pests and Diseases*:59-66, British Crop Protection Council, England (1981).
Moellenbeck, D.J., et al., "Insecticidal proteins from *Bacillus thuringiensis* protect corn from corn rootworms," *nature biotechnology 19*:668-672, Nature Publishing Group, England (2001).

Scheltes, P., et al., "Field Data on PH 70-23, A Novel Benzoylphenylurea Controlling Mites and Insects in a Range of Crops," *Brighton Crop Protection Conference—Pests and Diseases*:559-666, British Crop Protection Council, England (1988).
Schnepf, H.E., et al., "Characterization of Cry34/Cry35 Binary Insecticidal Proteins from Diverse *Bacillus thuringiensis* Strain Collections," *Appl. Environ. Microbiol.* 71(4):1765-1774, American Society for Microbiology, United States (2005).
Shah, D.M., et al., "Engineering Herbicide Tolerance in Transgenic Plants," *Science 233*:478-481, American Society for the Advancement of Science, United States (1986).
Tranel, P.J. and Wright, T.R., "Resistance of weeds to ALS-inhibiting herbicides: what have we learned?" *Weed Science 50*:700-712, Weed Science Society of America, United States (2002).
English Langauge Abstract of WIPO Patent Publication No. WO 99/57965 A1, European Patent Office, Espacenet Database (1999).
English Langauge Abstract of WIPO Patent Publication No. WO 01/14569 A2, European Patent Office, Espacenet Database (2001).
English Langauge Abstract of Chinese Patent Publication No. CN 1313276 A, European Patent Office, Espacenet Database (2001).
English Langauge Abstract of Japanese Patent Publication No. JP 2006-304779 A, European Patent Office, Espacenet Database (2006).
English Langauge Abstract of WIPO Patent Publication No. WO 2007/112843 A1, European Patent Office, Espacenet Database (2007).
International Search Report for International Application No. PCT/EP2009/002169, European Patent Office, The Hague, Netherlands, mailed on Dec. 1, 2009.
Written Opinion of the International Searching Authority for International Application No. PCT/EP2009/002169, European Patent Office, Netherlands, mailed on Dec. 1, 2009.
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyraid in Canola (*Brassica napus*)," *Weed Tech.* 3:690-695, The Weed Science Society of America, United States (1989).
Blackshaw, R.E., et al., "Herbicide Combinations for Postemergent Weed Control in Safflower (*Carthamus tinctorius*)," *Weed Tech.* 4:97-104, The Weed Science Society of America, United States (1990).
Blouin, D.C., et al., "Analysis of Synergistic Effects of Herbicides Using Nonlinear Mixed-Model Methodology," *Weed Tech.* 18:464-472, The Weed Science Society of America, United States (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).
Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).
Burke, I.C., et al., "CGA-362622 Antagonizes Annual Grass Control with Clethodim," *Weed Tech.* 16:749-754, The Weed Science Society of America, United States (2002).
Flint, J.L., et al., "Analyzing Herbicide Interactions: A Statistical Treatment of Colby's Method," Weed Tech. 2:304-309, The Weed Science Society of America, United States (1988).
Gillespie, G.R. and Nalewaja, J.D., "Wheat (*Triticum aestivum*) Response to Triallate Plus Chlorsulfuron," *Weed Tech.* 3:20-23, The Weed Science Society of America, United States (1989).
Green, J.M., et al., "Metribuzin and Clorimuron Mixtures for Preemergence Broadleaf Weed Control in Soybeans, *Glycine max*," *Weed Tech.* 2:355-363, The Weed Science Society of America, United States (1988).
Harker, K.N. and O'Sullivan, A., "Synergistic Mixtures of Sethoxydim and Fluazifop on Annual Grass Weeds," *Weed Tech.* 5:310-316, The Weed Science Society of America, United States (1991).
Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

(56) References Cited

OTHER PUBLICATIONS

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America, United States (2002).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic and Antagonistic Effects," *Weed Science* 23:4-6, The Weed Science Society of America, United States (1975).

Salzman, F.P. and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, A Graphic Representation of Synergism in Pesticides," *Neth. J. Plant Path.* 70:73-80, Springer, Germany (1964).

Wehtje, G., and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).

Zhang, W., et al., "Fenoxaprop Interactions for Barnyardgrass (*Echinochloa crus-galli*) Control in Rice," *Weed Tech.* 19:293-297, The Weed Science Society of America, United States (2005).

\* cited by examiner

ACTIVE INGREDIENT COMBINATIONS HAVING INSECTICIDAL AND ACARICIDAL PROPERTIES

The present invention relates to novel active compound combinations comprising, firstly, at least one known compound of the formula (I) and, secondly, at least one further known active compound from the class of the chitin synthesis inhibitors, the molting hormone agonists or other classes, which combinations are highly suitable for controlling animal pests such as insects and unwanted acarids.

The invention also relates to methods for controlling animal pests on plants and seed, to the use of the active compound combinations according to the invention for treating seed, to a method for protecting seed and last but not least to the seed treated with the active compound combinations according to the invention.

It is already known that compounds of the formula (I)

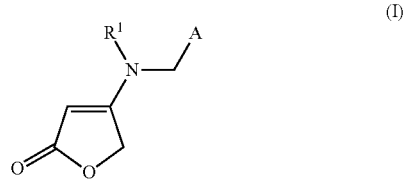

(I)

in which

A represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, or A represents a pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl radical which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine) or $C_1$-$C_3$-alkylsulphonyl (which is optionally substituted by fluorine and/or chlorine), or A represents a radical

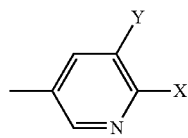

in which

X represents halogen, alkyl or haloalkyl,

Y represents halogen, alkyl, haloalkyl, haloalkoxy, azido or cyano and $R^1$ represents alkyl, haloalkyl, alkenyl, haloalkenyl, alkynyl, cycloalkyl, cycloalkylalkyl, halocycloalkyl, alkoxy, alkoxyalkyl or halocycloalkylalkyl, have insecticidal action (cf. EP 0 539 588, WO 2007/115643 A1, WO 2007/115644 A1 and WO 2007/115646 A1).

Furthermore, it is known that certain active compounds from the class of the chitin synthesis inhibitors, the molting hormone agonists or other classes have insecticidal and acaricidal properties. These compounds have been disclosed in published patent specifications and scientific publications. The insecticidal compounds described herein from the class of the chitin synthesis inhibitors, the molting hormone agonists or other classes are commercially available as individual active compounds in compositions for controlling animal pests. These compounds and compositions have been described in handbooks such as "The Pesticide Manual, 14th edition, C. D. S. Thomlin (Ed.), British Crop Protection Council, Surrey, UK, 2006", which is hereby incorporated by reference with respect to most of the active compounds disclosed herein from the class of the chitin synthesis inhibitors, the molting hormone agonists or other classes. The active compounds which are neither commercially available nor listed in the "Pesticide Manual" are identified by IUPAC number and/or structural formula.

The activity of the insecticidal compounds of the formula (I) or the active compounds from the class of the chitin synthesis inhibitors, the molting hormone agonists or other classes is generally good. However, in particular at low application rates and in the case of certain pests, they do not always meet the demands of agricultural practice, and there is still a need for economically efficient and ecologically safe pest control.

Further demands on insecticidal compounds include the reduction of the dosage rate; a substantial broadening of the spectrum of pests that can be controlled, including resistant pests; increased safety in use; reduced phytotoxicity and thus better tolerance by plants; the control of pests in their different development stages; better behaviour during production of the insecticidal compounds, for example during grinding or mixing, during their storage or during their use; a very advantageous biocidal spectrum, even at low rates of concentration, while being well tolerated by warm-blooded organisms, fish and plants; and achievement of additional effect, for example an algicidal, anthelmintic, avicidal, bactericidal, fungicidal, molluscicidal, nematicidal, plant-activating, rodenticidal or virucidal action.

Further specific demands on insecticidal compounds to be used on vegetative and generative plant propagation material include negligible phytotoxicity when applied to the seed and plant propagation material, compatibility with soil conditions (for example with regard to binding of the compound to the soil), systemic activity in the plant, no negative impact on germination, and efficacy during the lifecycle of the pest in question.

The object of the invention is to meet one or more of the demands mentioned above, such as, for example, the reduction of the dosage rate, a broadening of the spectrum of pests that can be controlled, including resistant pests, and in particular the specific demands for the applicability on vegetative and generative plant propagation material.

It has now been found that combinations of at least one compound of the formula (I), with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded, and at least one compound from the group of the active compounds 1 to 22 listed individually below from the class of the chitin synthesis inhibitors, the molting hormone agonists or other classes are synergistically active and are suitable for controlling animal pests.

Specifically, the following compounds 1 to 22 from the class of the chitin synthesis inhibitors, the molting hormone agonists or other classes may be mentioned:

a) inhibitors of chitin biosynthesis, for example benzoylureas such as 1. chlorfluazuron (known from DE-A 28 18 830)

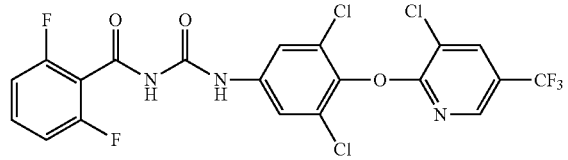 [SMILES: O=C(NC(=O)c1c(F)cccc1F)Nc1cc(Cl)c(Oc2ncc(C(F)(F)F)cc2Cl)c(Cl)c1]

2. diflubenzuron (known from DE-A 21 23 236)

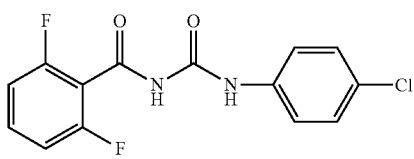 [SMILES: O=C(NC(=O)c1c(F)cccc1F)Nc1ccc(Cl)cc1]

3. lufenuron (known from EP-A 0 179 022)

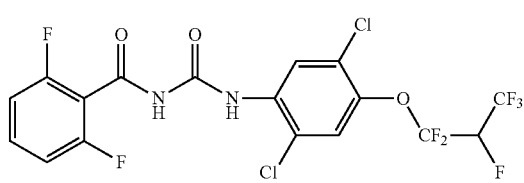

4. teflubenzuron (known from EP-A 0 052 833)

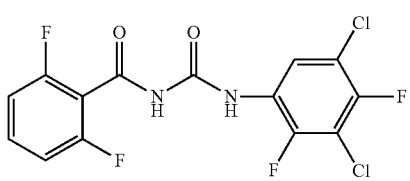 [SMILES: O=C(NC(=O)c1c(F)cccc1F)Nc1cc(Cl)c(F)c(Cl)c1F]

5. triflumuron (known from DE-A 26 01 780)

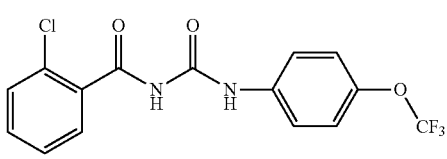 [SMILES: O=C(NC(=O)c1ccccc1Cl)Nc1ccc(OC(F)(F)F)cc1]

6. novaluron (known from U.S. Pat. No. 4,980,376)

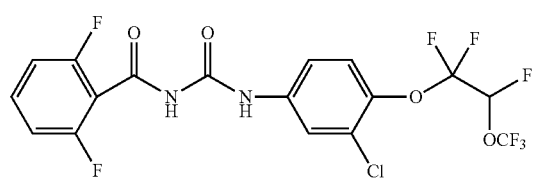 [SMILES: O=C(NC(=O)c1c(F)cccc1F)Nc1ccc(OC(F)(F)C(F)OC(F)(F)F)c(Cl)c1]

7. hexaflumuron (known from EP-A 0 071 279)

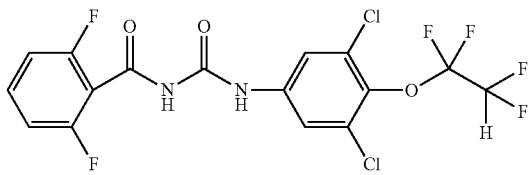 [SMILES: O=C(NC(=O)c1c(F)cccc1F)Nc1cc(Cl)c(OC(F)(F)C(F)F)c(Cl)c1]

8. bistrifluron (DBI-3204) (known from WO 98/00394)

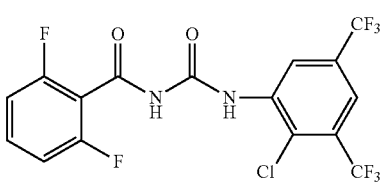 [SMILES: O=C(NC(=O)c1c(F)cccc1F)Nc1cc(C(F)(F)F)cc(C(F)(F)F)c1Cl]

9. flufenoxuron (known from EP-A 0 161 019)

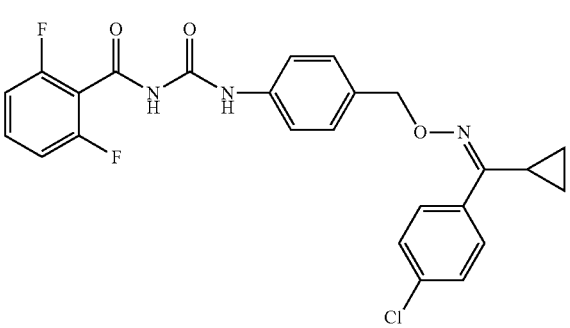 [SMILES: O=C(NC(=O)c1c(F)cccc1F)Nc1ccc(CO/N=C(\c2ccc(Cl)cc2)C2CC2)cc1]

10. flucycloxuron (known from P. Scheltes, T. W. Hofman, A. C. Grosscurt, BCPC Conf. Pests Dis. 1988, 2, 559-666, EP-A 00117320)

11. noviflumuron (known from WO 9819542A1, 1998)

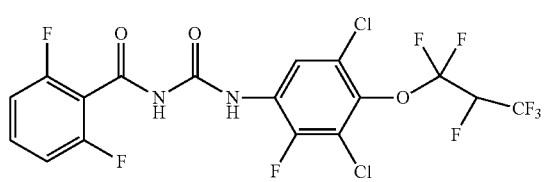 [SMILES: O=C(NC(=O)c1c(F)cccc1F)Nc1cc(Cl)c(OC(F)(F)C(F)C(F)(F)F)c(Cl)c1F]

12. fluazuron (known from EP-A 00079311)

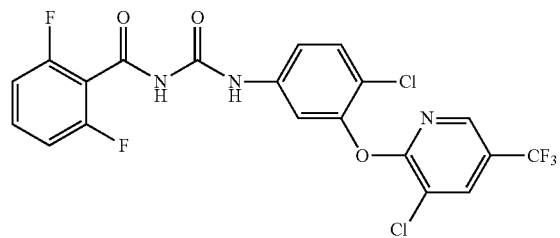 [SMILES: O=C(NC(=O)c1c(F)cccc1F)Nc1ccc(Cl)c(Oc2ncc(C(F)(F)F)cc2Cl)c1]

b) inhibitors of chitin biosynthesis such as
13. buprofezin (known from *Proc. Br. Crop Prot. Conf.— Pests Dis.*, 1981, 1, 59)

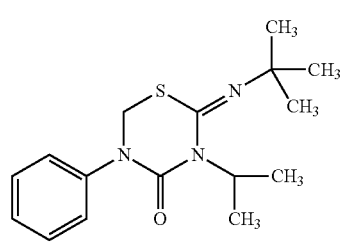 [SMILES: CC(C)N1C(=O)N(c2ccccc2)CSC1=NC(C)(C)C]

c) molting disruptors such as
14. cyromazine (known from GB-A 1 587 573)

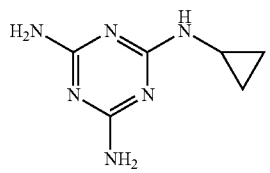 [SMILES: Nc1nc(N)nc(NC2CC2)n1]

d) juvenile hormone mimetics such as
15. pyriproxifen (known from GB-A 2 140 010)

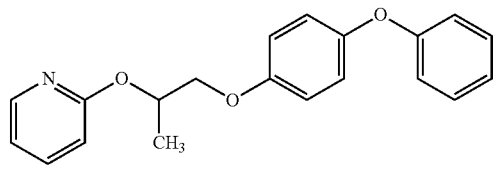 [SMILES: CC(COc1ccc(Oc2ccccc2)cc1)Oc1ccccn1]

16. diofenolan (known from DE 2 655 910)

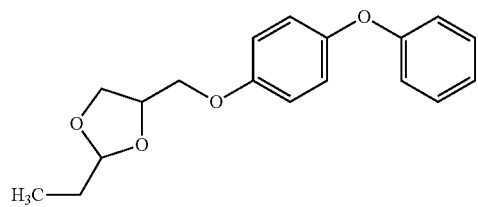 [SMILES: CCC1OCC(COc2ccc(Oc3ccccc3)cc2)O1]

17. fenoxycarb (known from EP 0 004 334)

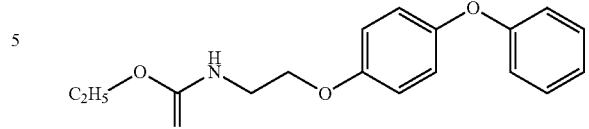

e) molting hormone (ecdysone) agonists, for example diacyl-hydrazines such as
18. tebufenozide (known from U.S. Pat. No. 4,985,461)

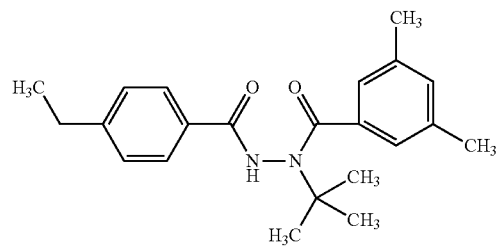 [SMILES: CCc1ccc(C(=O)NN(C(=O)c2cc(C)cc(C)c2)C(C)(C)C)cc1]

19. methoxyfenozide (known from U.S. Pat. No. 5,344,958)

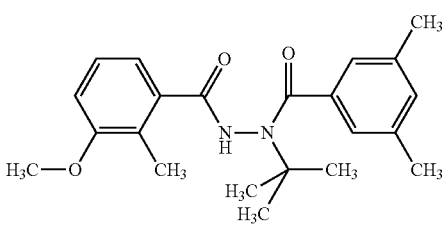

20. chromafenozide (known from EP 00496342)

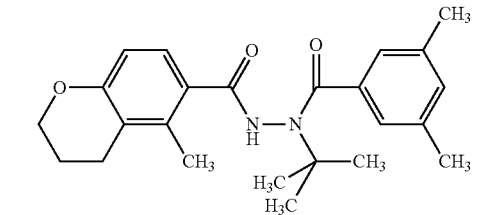 [SMILES: Cc1cc(C)cc(C(=O)N(NC(=O)c2ccc3c(c2C)CCCO3)C(C)(C)C)c1]

21. halofenozide (known from EP 228 564)

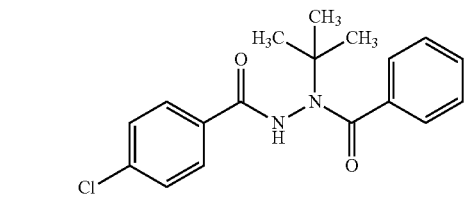 [SMILES: CC(C)(C)N(NC(=O)c1ccc(Cl)cc1)C(=O)c1ccccc1]

22. 2,3-dihydro-2,7-dimethyl-6-benzofurancarboxylic acid 2-(3,5-dimethylbenzoyl)-2-(1,1-dimethylethyl)hydrazide (JS 118) (known from CN-Pat. 1313276)

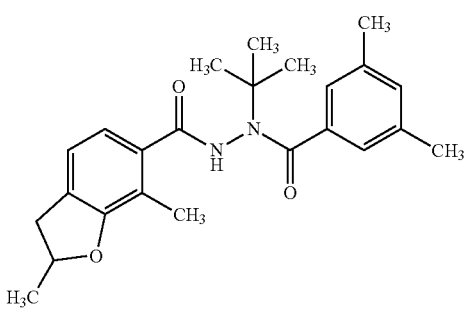

Surprisingly, the insecticidal and acaricidal action of the active compound combinations according to the invention considerably exceeds the total of the actions of the individual active compounds. A true synergistic effect which could not have been predicted exists, not just a complementation of action.

The synergistic action of the active compound combinations according to the invention of a compound of the formula (I) and an active compound from the class of the chitin synthesis inhibitors, the molting hormone agonists or other classes broadens the range of action of the compound of the formula (I) and the active compound from the class of the chitin synthesis inhibitors, the molting hormone agonists or other classes primarily by a reduction of the dosage rate and by broadening the spectrum of pests that can be controlled. Thus, using the active compound combination according to the invention of a compound of the formula (I) and an active compound from the class of the chitin synthesis inhibitors, the molting hormone agonists or other classes, it is still possible to achieve a high degree of pest control, even in cases where the individual compounds of the active compound combinations according to the invention have only insufficient activity at the low application rates used.

In addition to the synergistic action described above, the active compound combinations according to the invention may show other surprising advantages including increased safety in use; reduced phytotoxicity and thus better tolerance by plants, the control of pests in their different development stages; better behaviour during production of the insecticidal compounds, for example during grinding or mixing, during their storage or during their use; a very advantageous biocidal spectrum, even at low rates of concentration, while being well tolerated by warm-blooded organisms, fish and plants; and achievement of an additional effect, for example an algicidal, anthelmintic, avicidal, bactericidal, fungicidal, molluscicidal, nematicidal, plant-activating, rodenticidal or virucidal action.

Furthermore, surprisingly, it has been found that the active compound combinations according to the invention are particularly suitable for protecting seeds and/or seedlings and leaves from a plant grown from the seeds against damage by pests. Thus, the active compound combinations according to the invention have negligible phytotoxicity when applied to the plant propagation material, compatibility with soil conditions (for example with regard to binding of the compound to the soil), systemic activity in the plant, no negative impact on germination, and efficacy during the lifecycle of the pest in question.

The active compound combinations according to the invention comprise, in addition to at least one compound of the formula (I), at least one of the active compounds 1 to 22 listed individually above from the class of the chitin synthesis inhibitors, the molting hormone agonists or other classes.

The active compound combinations according to the invention preferably comprise exactly one compound of the formula (I) and exactly one of the active compounds 1 to 22 listed individually above from the class of the chitin synthesis inhibitors, the molting hormone agonists or other classes. Preference is furthermore given to active compound combinations comprising one compound of the formula (I) and two of the active compounds 1 to 22 listed individually above from the class of the chitin synthesis inhibitors, the molting hormone agonists or other classes. Preference is furthermore given to mixtures comprising two compounds of the formula (I) and one of the active compounds 1 to 22 listed individually above from the class of the chitin synthesis inhibitors, the molting hormone agonists or other classes.

Preferred sub-groups of the compounds of the formula (I) mentioned above in the active compound combinations according to the invention with at least one of the active compounds 1 to 22 listed individually above from the class of the chitin synthesis inhibitors, the molting hormone agonists or other classes are listed below, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded.

A preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromo-pyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl or 5-difluoromethyl-6-iodopyrid-3-yl.

$R^1$ preferably represents optionally fluorine-substituted $C_1$-$C_5$-alkyl, $C_2$-$C_5$-alkenyl, $C_3$-$C_5$-cycloalkyl, $C_3$-$C_5$-cycloalkylalkyl or $C_1$-$C_5$-alkoxy.

A particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl radical.

$R^1$ particularly preferably represents methyl, methoxy, ethyl, propyl, vinyl, allyl, propargyl, cyclopropyl, 2-fluoroethyl, 2,2-difluoroethyl or 2-fluorocyclopropyl.

A very particularly preferably represents the 6-fluoropyrid-3-yl, 6-chloropyrid-3-yl, 6-bromopyrid-3-yl, 5-fluoro-6-chloropyrid-3-yl, 2-chloro-1,3-thiazol-5-yl or 5,6-dichloropyrid-3-yl radical.

$R^1$ very particularly preferably represents methyl, cyclopropyl, methoxy, 2-fluoroethyl or 2,2-difluoroethyl.

A most preferably represents the 6-chloropyrid-3-yl or 5-fluoro-6-chloropyrid-3-yl radical.

$R^1$ most preferably represents methyl, 2-fluoroethyl or 2,2-difluoroethyl.

In a special group of compounds of the formula (I), A represents 6-chloropyrid-3-yl.

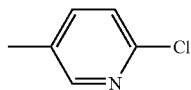

In a further special group of compounds of the formula (1), A represents 6-bromopyrid-3-yl.

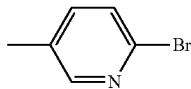

In a further special group of compounds of the formula (I), A represents 6-chloro-1,4-pyridazin-3-yl.

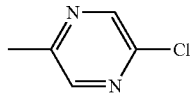

In a further special group of compounds of the formula (I), A represents 2-chloro-1,3-thiazol-5-yl.

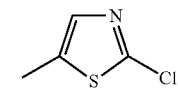

In a further special group of compounds of the formula (I), A represents 5-fluoro-6-chloropyrid-3-yl.

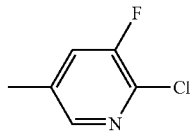

In a further special group of compounds of the formula (I), A represents 5-fluoro-6-bromopyrid-3-yl.

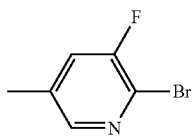

In a further special group of compounds of the formula (I), A represents 5,6-dichloropyrid-3-yl.

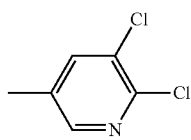

In a further special group of compounds of the formula (I), $R^1$ represents methyl.

In a further special group of compounds of the formula (I), $R^1$ represents ethyl.

In a further special group of compounds of the formula (I), $R^1$ represents cyclopropyl.

In a further special group of compounds of the formula (I), $R^1$ represents 2-fluoroethyl.

In a further special group of compounds of the formula (I), $R^1$ represents 2,2-difluoroethyl.

The abovementioned general or preferred radical definitions or illustrations can be combined with one another as desired, i.e. including combinations between the respective preferred ranges.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (1) which contain a combination of the meanings listed above as being very particularly preferred.

A preferred sub-group of the compounds of the formula (I) are those of the formula (I-a)

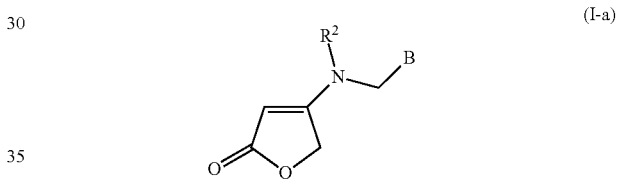

in which

B represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine, or methyl or represents pyrazin-3-yl or represents 2-chloropyrazin-5-yl or represents 1,3-thiazol-5-yl which is optionally substituted in the 2-position by chlorine or methyl, $R^2$ represents haloalkyl, haloalkenyl, halocycloalkyl or halocycloalkylalkyl.

Preferred substituents or ranges of the radicals mentioned in the formula (I-a) shown above and below are illustrated below:

B preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

$R^2$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

B particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl radical.

$R^2$ particularly preferably represents 2-fluoroethyl, 2,2-difluoroethyl, 2-fluorocyclopropyl.

B very particularly preferably represents the 6-chloropyrid-3-yl radical.

$R^2$ very particularly preferably represents 2-fluoroethyl or 2,2-difluoroethyl.

In a special group of compounds of the formula (I-a), B represents 6-chloropyrid-3-yl.

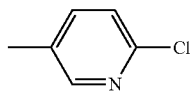

In a further special group of compounds of the formula (I-a), B represents 6-bromopyrid-3-yl.

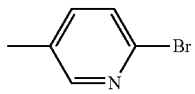

In a further special group of compounds of the formula (I-a), B represents 6-chloro-1,4-pyridazin-3-yl.

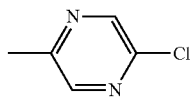

In a further special group of compounds of the formula (I-a), $R^2$ represents 2-fluoroethyl.

In a further special group of compounds of the formula (I-a), $R^2$ represents 2,2-difluoroethyl.

A further preferred sub-group of the compounds of the formula (I) are those of the formula (I-b)

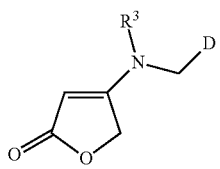

(I-b)

in which
D represents a radical

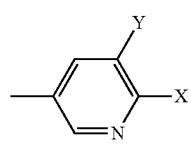

in which
X and Y have the meanings given above,
$R^3$ represents hydrogen, alkyl, alkenyl, alkynyl, cycloalkyl or alkoxy.

Preferred substituents or ranges of the radicals mentioned in the formula (I-b) shown above and below are illustrated below:

D preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^3$ preferably represents $C_1$-$C_4$-alkyl, $C_2$-$C_4$-alkenyl, $C_2$-$C_4$-alkynyl or $C_3$-$C_4$-cycloalkyl.

D particularly preferably represents 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^3$ particularly preferably represents $C_1$-$C_4$-alkyl.

D very particularly preferably represents 5-fluoro-6-chloropyrid-3-yl or 5-fluoro-6-bromopyrid-3-yl.

$R^3$ very particularly preferably represents methyl, ethyl, propyl, vinyl, allyl, propargyl or cyclopropyl.

D most preferably represents 5-fluoro-6-chloropyrid-3-yl.

$R^3$ most preferably represents methyl or cyclopropyl.

In a further special group of compounds of the formula (I-b), D represents 5-fluoro-6-chloropyrid-3-yl.

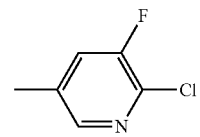

In a further special group of compounds of the formula (I-b), D represents 5,6-dichloropyrid-3-yl.

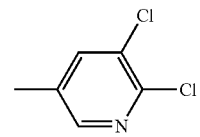

In a further special group of compounds of the formula (I-b), D represents 5-bromo-6-chloropyrid-3-yl.

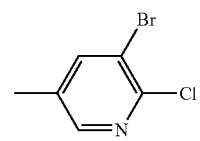

In a further special group of compounds of the formula (I-b), D represents 5-methyl-6-chloropyrid-3-yl.

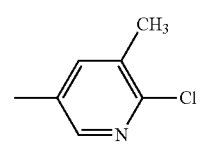

In a further special group of compounds of the formula (I-b), D represents 5-fluoro-6-bromopyrid-3-yl.

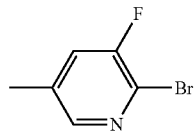

In a further special group of compounds of the formula (I-b), D represents 5-chloro-6-bromopyrid-3-yl.

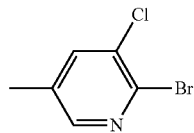

In a further special group of compounds of the formula (I-b), D represents 5-chloro-6-iodopyrid-3-yl.

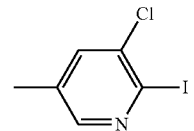

In a further special group of compounds of the formula (I-b), $R^3$ represents methyl.

In a further special group of compounds of the formula (I-b), $R^3$ represents ethyl.

In a further special group of compounds of the formula (I-b), $R^3$ represents cyclopropyl.

A further preferred sub-group of the compounds of the formula (I) are those of the formula (I-c)

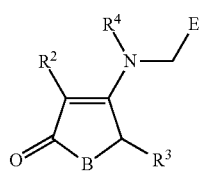

in which
E represents a radical

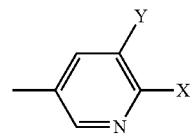

in which
X and Y have the meanings given above and
$R^4$ represents haloalkyl, haloalkenyl, halocycloalkyl or halocycloalkylalkyl.

Preferred substituents or ranges of the radicals mentioned in the formula (I-c) shown above and below are illustrated below:

E preferably represents one of the radicals 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl, 5-difluoromethyl-6-iodopyrid-3-yl.

$R^4$ preferably represents fluorine-substituted $C_1$-$C_5$-alkyl, $C_2$-$C_5$-alkenyl, $C_3$-$C_5$-cycloalkyl or $C_3$-$C_5$-cycloalkylalkyl.

E particularly preferably represents 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl or 5-difluoromethyl-6-chloropyrid-3-yl.

$R^4$ particularly preferably represents 2-fluoroethyl, 2,2-difluoroethyl, 2-fluorocyclopropyl.

E very particularly preferably represents 5-fluoro-6-chloropyrid-3-yl.

$R^4$ very particularly preferably represents 2-fluoroethyl or 2,2-difluoroethyl.

In a further special group of compounds of the formula (I-c), E represents 5-fluoro-6-chloropyrid-3-yl.

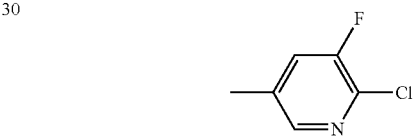

In a further special group of compounds of the formula (I-c), E represents 5,6-dichloropyrid-3-yl.

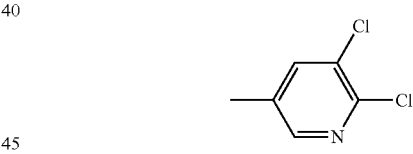

In a further special group of compounds of the formula (I-c), E represents 5-bromo-6-chloropyrid-3-yl.

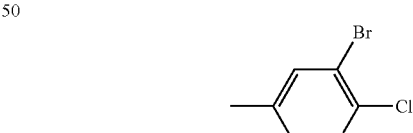

In a further special group of compounds of the formula (I-c), E represents 5-methyl-6-chloropyrid-3-yl.

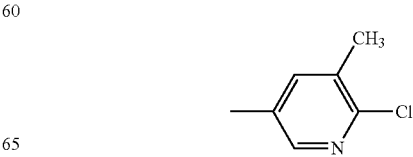

In a further special group of compounds of the formula (I-c), E represents 5-fluoro-6-bromopyrid-3-yl.

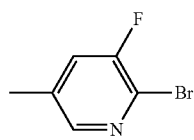

In a further special group of compounds of the formula (I-c), E represents 5-chloro-6-bromopyrid-3-yl.

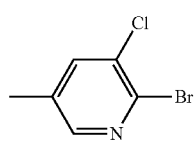

In a further special group of compounds of the formula (I-c), E represents 5-chloro-6-iodopyrid-3-yl.

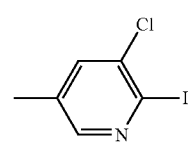

In a further special group of compounds of the formula (I-c), $R^4$ represents 2-fluoroethyl.

In a further special group of compounds of the formula (I-c), $R^4$ represents 2,2-difluoroethyl.

A preferred sub-group of the compounds of the formula (I) are those of the formula (I-d)

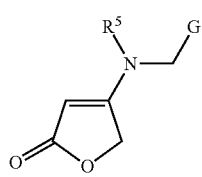

(I-d)

in which

G represents pyrid-2-yl or pyrid-4-yl or represents pyrid-3-yl which is optionally substituted in the 6-position by fluorine, chlorine, bromine, methyl, trifluoromethyl or trifluoromethoxy or represents pyridazin-3-yl which is optionally substituted in the 6-position by chlorine or methyl or represents pyrazin-3-yl or represents 2-chloropyrazin-5-yl or represents 1,3-thiazol-5-yl which is optionally substituted in the 2-position by chlorine or methyl, and $R^5$ represents $C_1$-$C_4$-alkyl, $C_2$-$C_4$-alkenyl, $C_2$-$C_4$-alkynyl, $C_3$-$C_4$-cycloalkyl or $C_1$-$C_4$alkoxy, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded.

Preferred substituents or ranges of the radicals mentioned in the formula (I-d) shown above and below are illustrated below:

G preferably represents 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl.

$R^5$ preferably represents $C_1$-$C_4$-alkyl, $C_1$-alkoxy, $C_2$-$C_4$-alkenyl, $C_2$-$C_4$-alkynyl or $C_3$-$C_4$-cycloalkyl.

G particularly preferably represents the 6-fluoropyrid-3-yl, 6-chloropyrid-3-yl, 6-bromopyrid-3-yl, 6-chloro-1,4-pyridazin-3-yl, 2-chloro-1,3-thiazol-5-yl radical.

$R^5$ particularly preferably represents methyl, methoxy, ethyl, propyl, vinyl, allyl, propargyl or cyclopropyl.

G very particularly preferably represents the 6-chloropyrid-3-yl radical.

$R^5$ very particularly preferably represents methyl or cyclopropyl.

In a special group of compounds of the formula (I-d), G represents 6-chloropyrid-3-yl.

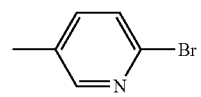

In a further special group of compounds of the formula (I-d), G represents 6-bromopyrid-3-yl.

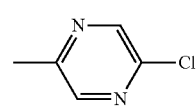

In a further special group of compounds of the formula (I-d), G represents 6-chloro-1,4-pyridazin-3-yl.

In a further special group of compounds of the formula (I-d), G represents 2-chloro-1,3-thiazol-5-yl.

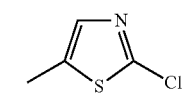

In a further special group of compounds of the formula (I-d), G represents 6-fluoropyrid-3-yl.

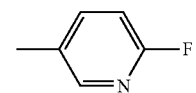

In a further special group of compounds of the formula (I-d), G represents 6-trifluoromethylpyrid-3-yl.

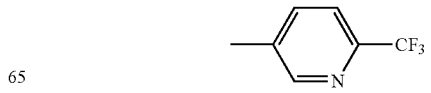

In a further special group of compounds of the formula (I-d), G represents 6-fluoropyrid-3-yl.

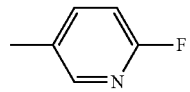

In a further special group of compounds of the formula (I-d), $R^5$ represents methyl.

In a further special group of compounds of the formula (I-d), $R^5$ represents cyclopropyl.

Specific mention may be made of the following compounds of the general formula (I):

compound (I-1), 4-{[(6-bromopyrid-3-yl)methyl](2-fluoroethyl)amino}furan-2(5H)-one, has the formula

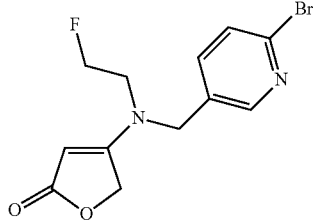 [SMILES: O=C1C=C(N(CCF)Cc2ccc(Br)nc2)CO1]

and is known from WO 2007/115644 A1.

Compound (I-2), 4-{[(6-fluoropyrid-3-yl)methyl](2,2-difluoroethyl)amino}furan-2(5H)-one, has the formula

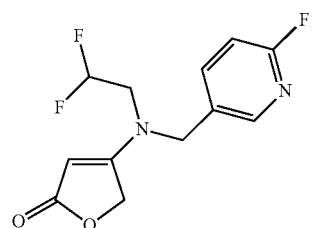

and is known from WO 2007/115644 A1.

Compound (I-3), 4-{[(2-chloro-1,3-thiazol-5-yl)methyl](2-fluoroethyl)amino}furan-2(5H)-one, has the formula

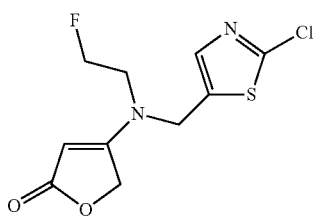 [SMILES: O=C1C=C(N(CCF)Cc2cnc(Cl)s2)CO1]

and is known from WO 2007/115644 A1.

Compound (I-4), 4-{[(6-chloropyrid-3-yl)methyl](2-fluoroethyl)amino}furan-2(5H)-one, has the formula

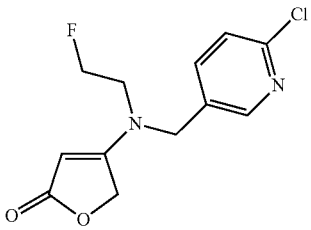 [SMILES: O=C1C=C(N(CCF)Cc2ccc(Cl)nc2)CO1]

and is known from WO 2007/115644 A1.

Compound (I-5), 4-{[(6-chloropyrid-3-yl)methyl](2,2-difluoroethyl)amino}furan-2(5H)-one, has the formula

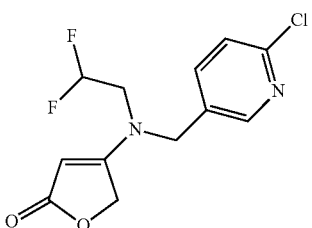

and is known from WO 2007/115644 A1.

Compound (I-6), 4-{[(6-chloro-5-fluorpyrid-3-yl)methyl](methyl)amino}furan-2(5H)-one, has the formula

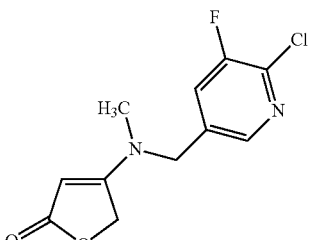

and is known from WO 2007/115643 A1.

Compound (I-7), 4-{[(5,6-dichloropyrid-3-yl)methyl](2-fluoroethyl)amino}furan-2(5H)-one, has the formula

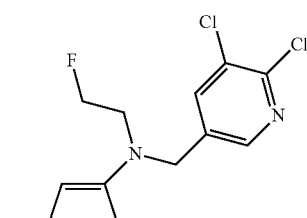

and is known from WO 2007/115646 A1.

Compound (I-8), 4-{[(6-chloro-5-fluoropyrid-3-yl)methyl](cyclopropyl)amino}furan-2(5H)-one, has the formula

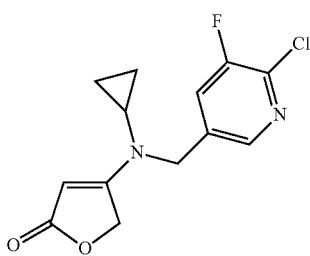 [SMILES: O=C1C=C(N(Cc2cnc(Cl)c(F)c2)C2CC2)CO1]

and is known from WO 2007/115643 A1.

The active compound combinations according to the invention preferably comprise at least one of the compounds of the formula (I) selected from the group consisting of the compounds of the formulae (I-a), (I-b), (I-c) and (I-d) shown above, with the proviso that 4-{[(6-chloropyrid-3-yl)methyl](methyl)amino}furan-2(5H)-one and 4-{[(6-chloropyrid-3-yl)methyl](cyclo-propyl)amino}furan-2(5H)-one are excluded, and one of the active compounds 1 to 22 listed individually above from the class of the chitin synthesis inhibitors, the molting hormone agonists or other classes.

The active compound combinations according to the invention furthermore preferably comprise at least one of the compounds of the formula (I) selected from the group consisting of the compounds of the formulae (I-a), (I-b) and (I-c) shown above and one of the active compounds 1 to 22 listed individually above from the class of the chitin synthesis inhibitors, the molting hormone agonists or other classes.

Particularly preferably, the active compound combinations according to the invention comprise at least one of the compounds of the formula (1) in which A is selected from among the radicals 6-fluoropyrid-3-yl, 6-chloropyrid-3-yl, 6-bromopyrid-3-yl, 5-fluoro-6-chloropyrid-3-yl, 2-chloro-1,3-thiazol-5-yl and 5,6-dichloropyrid-3-yl and $R^1$ is selected from among the radicals methyl, cyclopropyl, methoxy, 2-fluoroethyl and 2,2-difluoroethyl, with the proviso that 4-{[(6-chloropyrid-3-yl)methyl](methyl)amino}furan-2(5H)-one and 4-{[(6-chloropyrid-3-yl)methyl](cyclopropyl)amino}furan-2(5H)-one are excluded, and one of the active compounds 1 to 22 listed individually above from the class of the chitin synthesis inhibitors, the molting hormone agonists or other classes.

Very particularly preferably, the active compound combinations according to the invention comprise at least one compound of the formula (I) selected from the group consisting of the compounds of the formulae (I-1), (I-2), (I-3), (I-4), (I-5), (I-6), (I-7) and (I-8) shown above, and one of the active compounds 1 to 22 listed individually above from the class of the chitin synthesis inhibitors, the molting hormone agonists or other classes.

This gives the combinations listed in Table 1, where each combination per se is a very particularly preferred embodiment of the invention.

TABLE 1

| No. of the active compound combination | Compound of the formula I | | Active compound |
|---|---|---|---|
| 1-1 | I-1 | and | 1 (chlorfluazuron) |
| 1-2 | I-1 | and | 2 (diflubenzuron) |
| 1-3 | I-1 | and | 3 (lufenuron) |
| 1-4 | I-1 | and | 4 (teflubenzuron) |

TABLE 1-continued

| No. of the active compound combination | Compound of the formula I | | Active compound |
|---|---|---|---|
| 1-5 | I-1 | and | 5 (triflumuron) |
| 1-6 | I-1 | and | 6 (novaluron) |
| 1-7 | I-1 | and | 7 (hexaflumuron) |
| 1-8 | I-1 | and | 8 (bistrifluron) |
| 1-9 | I-1 | and | 9 (flufenoxuron) |
| 1-10 | I-1 | and | 10 (flucycloxuron) |
| 1-11 | I-1 | and | 11 (noviflumuron) |
| 1-12 | I-1 | and | 12 (fluazuron) |
| 1-13 | I-1 | and | 13 (buprofezin) |
| 1-14 | I-1 | and | 14 (cyromazine) |
| 1-15 | I-1 | and | 15 (pyriproxifen) |
| 1-16 | I-1 | and | 16 (diofenolan) |
| 1-17 | I-1 | and | 17 (fenoxycarb) |
| 1-18 | I-1 | and | 18 (tebufenozide) |
| 1-19 | I-1 | and | 19 (methoxyfenozide) |
| 1-20 | I-1 | and | 20 (chromafenozide) |
| 1-21 | I-1 | and | 21 (halofenozide) |
| 1-22 | I-1 | and | 22 (JS 118) |

Furthermore, the combinations listed in Table 2 are obtained, where each combination per se is a preferred embodiment of the invention.

TABLE 2

| No. of the active compound combination | Compound of the formula I | | Active compound |
|---|---|---|---|
| 2-1 | I-2 | and | 1 (chlorfluazuron) |
| 2-2 | I-2 | and | 2 (diflubenzuron) |
| 2-3 | I-2 | and | 3 (lufenuron) |
| 2-4 | I-2 | and | 4 (teflubenzuron) |
| 2-5 | I-2 | and | 5 (triflumuron) |
| 2-6 | I-2 | and | 6 (novaluron) |
| 2-7 | I-2 | and | 7 (hexaflumuron) |
| 2-8 | I-2 | and | 8 (bistrifluron) |
| 2-9 | I-2 | and | 9 (flufenoxuron) |
| 2-10 | I-2 | and | 10 (flucycloxuron) |
| 2-11 | I-2 | and | 11 (noviflumuron) |
| 2-12 | I-2 | and | 12 (fluazuron) |
| 2-13 | I-2 | and | 13 (buprofezin) |
| 2-14 | I-2 | and | 14 (cyromazine) |
| 2-15 | I-2 | and | 15 (pyriproxifen) |
| 2-16 | I-2 | and | 16 (diofenolan) |
| 2-17 | I-2 | and | 17 (fenoxycarb) |
| 2-18 | I-2 | and | 18 (tebufenozide) |
| 2-19 | I-2 | and | 19 (methoxyfenozide) |
| 2-20 | I-2 | and | 20 (chromafenozide) |
| 2-21 | I-2 | and | 21 (halofenozide) |
| 2-22 | I-2 | and | 22 (JS 118) |

Furthermore, the combinations listed in Table 3 are obtained, where each combination per se is a preferred embodiment of the invention.

TABLE 3

| No. of the active compound combination | Compound of the formula I | | Active compound |
|---|---|---|---|
| 3-1 | I-3 | and | 1 (chlorfluazuron) |
| 3-2 | I-3 | and | 2 (diflubenzuron) |
| 3-3 | I-3 | and | 3 (lufenuron) |
| 3-4 | I-3 | and | 4 (teflubenzuron) |

TABLE 3-continued

Active compound combination comprising

| No. of the active compound combination | Compound of the formula I | | Active compound |
|---|---|---|---|
| 3-5 | I-3 | and | 5 (triflumuron) |
| 3-6 | I-3 | and | 6 (novaluron) |
| 3-7 | I-3 | and | 7 (hexaflumuron) |
| 3-8 | I-3 | and | 8 (bistrifluron) |
| 3-9 | I-3 | and | 9 (flufenoxuron) |
| 3-10 | I-3 | and | 10 (flucycloxuron) |
| 3-11 | I-3 | and | 11 (noviflumuron) |
| 3-12 | I-3 | and | 12 (fluazuron) |
| 3-13 | I-3 | and | 13 (buprofezin) |
| 3-14 | I-3 | and | 14 (cyromazine) |
| 3-15 | I-3 | and | 15 (pyriproxifen) |
| 3-16 | I-3 | and | 16 (diofenolan) |
| 3-17 | I-3 | and | 17 (fenoxycarb) |
| 3-18 | I-3 | and | 18 (tebufenozide) |
| 3-19 | I-3 | and | 19 (methoxyfenozide) |
| 3-20 | I-3 | and | 20 (chromafenozide) |
| 3-21 | I-3 | and | 21 (halofenozide) |
| 3-22 | I-3 | and | 22 (JS 118) |

Furthermore, the combinations listed in Table 4 are obtained, where each combination per se is a preferred embodiment of the invention.

TABLE 4

Active compound combination comprising

| No. of the active compound combination | Compound of the formula I | | Active compound |
|---|---|---|---|
| 4-1 | I-4 | and | 1 (chlorfluazuron) |
| 4-2 | I-4 | and | 2 (diflubenzuron) |
| 4-3 | I-4 | and | 3 (lufenuron) |
| 4-4 | I-4 | and | 4 (teflubenzuron) |
| 4-5 | I-4 | and | 5 (triflumuron) |
| 4-6 | I-4 | and | 6 (novaluron) |
| 4-7 | I-4 | and | 7 (hexaflumuron) |
| 4-8 | I-4 | and | 8 (bistrifluron) |
| 4-9 | I-4 | and | 9 (flufenoxuron) |
| 4-10 | I-4 | and | 10 (flucycloxuron) |
| 4-11 | I-4 | and | 11 (noviflumuron) |
| 4-12 | I-4 | and | 12 (fluazuron) |
| 4-13 | I-4 | and | 13 (buprofezin) |
| 4-14 | I-4 | and | 14 (cyromazine) |
| 4-15 | I-4 | and | 15 (pyriproxifen) |
| 4-16 | I-4 | and | 16 (diofenolan) |
| 4-17 | I-4 | and | 17 (fenoxycarb) |
| 4-18 | I-4 | and | 18 (tebufenozide) |
| 4-19 | I-4 | and | 19 (methoxyfenozide) |
| 4-20 | I-4 | and | 20 (chromafenozide) |
| 4-21 | I-4 | and | 21 (halofenozide) |
| 4-22 | I-4 | and | 22 (JS 118) |

Furthermore, the combinations listed in Table 5 are obtained, where each combination per se is a preferred embodiment of the invention.

TABLE 5

Active compound combination comprising

| No. of the active compound combination | Compound of the formula I | | Active compound |
|---|---|---|---|
| 5-1 | I-5 | and | 1 (chlorfluazuron) |
| 5-2 | I-5 | and | 2 (diflubenzuron) |
| 5-3 | I-5 | and | 3 (lufenuron) |
| 5-4 | I-5 | and | 4 (teflubenzuron) |
| 5-5 | I-5 | and | 5 (triflumuron) |
| 5-6 | I-5 | and | 6 (novaluron) |
| 5-7 | I-5 | and | 7 (hexaflumuron) |
| 5-8 | I-5 | and | 8 (bistrifluron) |
| 5-9 | I-5 | and | 9 (flufenoxuron) |
| 5-10 | I-5 | and | 10 (flucycloxuron) |
| 5-11 | I-5 | and | 11 (noviflumuron) |
| 5-12 | I-5 | and | 12 (fluazuron) |
| 5-13 | I-5 | and | 13 (buprofezin) |
| 5-14 | I-5 | and | 14 (cyromazine) |
| 5-15 | I-5 | and | 15 (pyriproxifen) |
| 5-16 | I-5 | and | 16 (diofenolan) |
| 5-17 | I-5 | and | 17 (fenoxycarb) |
| 5-18 | I-5 | and | 18 (tebufenozide) |
| 5-19 | I-5 | and | 19 (methoxyfenozide) |
| 5-20 | I-5 | and | 20 (chromafenozide) |
| 5-21 | I-5 | and | 21 (halofenozide) |
| 5-22 | I-5 | and | 22 (JS 118) |

Furthermore, the combinations listed in Table 6 are obtained, where each combination per se is a preferred embodiment of the invention.

TABLE 6

Active compound combination comprising

| No. of the active compound combination | Compound of the formula I | | Active compound |
|---|---|---|---|
| 6-1 | I-6 | and | 1 (chlorfluazuron) |
| 6-2 | I-6 | and | 2 (diflubenzuron) |
| 6-3 | I-6 | and | 3 (lufenuron) |
| 6-4 | I-6 | and | 4 (teflubenzuron) |
| 6-5 | I-6 | and | 5 (triflumuron) |
| 6-6 | I-6 | and | 6 (novaluron) |
| 6-7 | I-6 | and | 7 (hexaflumuron) |
| 6-8 | I-6 | and | 8 (bistrifluron) |
| 6-9 | I-6 | and | 9 (flufenoxuron) |
| 6-10 | I-6 | and | 10 (flucycloxuron) |
| 6-11 | I-6 | and | 11 (noviflumuron) |
| 6-12 | I-6 | and | 12 (fluazuron) |
| 6-13 | I-6 | and | 13 (buprofezin) |
| 6-14 | I-6 | and | 14 (cyromazine) |
| 6-15 | I-6 | and | 15 (pyriproxifen) |
| 6-16 | I-6 | and | 16 (diofenolan) |
| 6-17 | I-6 | and | 17 (fenoxycarb) |
| 6-18 | I-6 | and | 18 (tebufenozide) |
| 6-19 | I-6 | and | 19 (methoxyfenozide) |
| 6-20 | I-6 | and | 20 (chromafenozide) |
| 6-21 | I-6 | and | 21 (halofenozide) |
| 6-22 | I-6 | and | 22 (JS 118) |

Furthermore, the combinations listed in Table 7 are obtained, where each combination per se is a preferred embodiment of the invention.

TABLE 7

Active compound combination comprising

| No. of the active compound combination | Compound of the formula I | | Active compound |
|---|---|---|---|
| 7-1 | I-7 | and | 1 (chlorfluazuron) |
| 7-2 | I-7 | and | 2 (diflubenzuron) |
| 7-3 | I-7 | and | 3 (lufenuron) |
| 7-4 | I-7 | and | 4 (teflubenzuron) |

TABLE 7-continued

Active compound combination comprising

| No. of the active compound combination | Compound of the formula I | | Active compound |
|---|---|---|---|
| 7-5 | I-7 | and | 5 (triflumuron) |
| 7-6 | I-7 | and | 6 (novaluron) |
| 7-7 | I-7 | and | 7 (hexaflumuron) |
| 7-8 | I-7 | and | 8 (bistrifluron) |
| 7-9 | I-7 | and | 9 (flufenoxuron) |
| 7-10 | I-7 | and | 10 (flucycloxuron) |
| 7-11 | I-7 | and | 11 (noviflumuron) |
| 7-12 | I-7 | and | 12 (fluazuron) |
| 7-13 | I-7 | and | 13 (buprofezin) |
| 7-14 | I-7 | and | 14 (cyromazine) |
| 7-15 | I-7 | and | 15 (pyriproxifen) |
| 7-16 | I-7 | and | 16 (diofenolan) |
| 7-17 | I-7 | and | 17 (fenoxycarb) |
| 7-18 | I-7 | and | 18 (tebufenozide) |
| 7-19 | I-7 | and | 19 (methoxyfenozide) |
| 7-20 | I-7 | and | 20 (chromafenozide) |
| 7-21 | I-7 | and | 21 (halofenozide) |
| 7-28 | I-7 | and | 22 (JS 118) |

Furthermore, the combinations listed in Table 8 are obtained, where each combination per se is a preferred embodiment of the invention.

TABLE 8

Active compound combination comprising

| No. of the active compound combination | Compound of the formula I | | Active compound |
|---|---|---|---|
| 8-1 | I-8 | and | 1 (chlorfluazuron) |
| 8-2 | I-8 | and | 2 (diflubenzuron) |
| 8-3 | I-8 | and | 3 (lufenuron) |
| 8-4 | I-8 | and | 4 (teflubenzuron) |
| 8-5 | I-8 | and | 5 (triflumuron) |
| 8-6 | I-8 | and | 6 (novaluron) |
| 8-7 | I-8 | and | 7 (hexaflumuron) |
| 8-8 | I-8 | and | 8 (bistrifluron) |
| 8-9 | I-8 | and | 9 (flufenoxuron) |
| 8-10 | I-8 | and | 10 (flucycloxuron) |
| 8-11 | I-8 | and | 11 (noviflumuron) |
| 8-12 | I-8 | and | 12 (fluazuron) |
| 8-13 | I-8 | and | 13 (buprofezin) |
| 8-14 | I-8 | and | 14 (cyromazine) |
| 8-15 | I-8 | and | 15 (pyriproxifen) |
| 8-16 | I-8 | and | 16 (diofenolan) |
| 8-17 | I-8 | and | 17 (fenoxycarb) |
| 8-18 | I-8 | and | 18 (tebufenozide) |
| 8-19 | I-8 | and | 19 (methoxyfenozide) |
| 8-20 | I-8 | and | 20 (chromafenozide) |
| 8-21 | I-8 | and | 21 (halofenozide) |
| 8-22 | I-8 | and | 22 (JS 118) |

If the active compounds are present in the active compound combinations according to the invention in certain weight ratios, the synergistic effect is particularly pronounced. However, the weight ratios of the active compounds in the active compound combinations can be varied within a relatively wide range. In general, the combinations according to the invention comprise an active compound of the formula (I) and one of the active compounds 1 to 22 listed individually above from the class of the chitin synthesis inhibitors, the molting hormone agonists or other classes in the following preferred and particularly preferred mixing ratios:

Preferred mixing ratio: 125:1 to 1:125

Particularly preferred mixing ratio: 25:1 to 1:25

The mixing ratios are based on weight ratios. The ratio is to be understood as meaning compound of the formula (I): active compound 1 to 22.

Further mixing ratios of the compound of the formula (I) to one of the active compounds 1 to 22 listed individually above from the class of the chitin synthesis inhibitors, the molting hormone agonists or other classes are specified below and are sorted according to increasing preference of the mixing ratios: 95:1 to 1:95, 95:1 to 1:90, 95:1 to 1:85, 95:1 to 1:80, 95:1 to 1:75, 95:1 to 1:70, 95:1 to 1:65, 95:1 to 1:60, 95:1 to 1:55, 95:1 to 1:50, 95:1 to 1:45, 95:1 to 1:40, 95:1 to 1:35, 95:1 to 1:30, 95:1 to 1:25, 95:1 to 1:20, 95:1 to 1:15, 95:1 to 1:10, 95:1 to 1:5, 95:1 to 1:4, 95:1 to 1:3, 95:1 to 1:2, 90:1 to 1:90, 90:1 to 1:95, 90:1 to 1:85, 90:1 to 1:80, 90:1 to 1:75, 90:1 to 1:70, 90:1 to 1:65, 90:1 to 1:60, 90:1 to 1:55, 90:1 to 1:50, 90:1 to 1:45, 90:1 to 1:40, 90:1 to 1:35, 90:1 to 1:30, 90:1 to 1:25, 90:1 to 1:20, 90:1 to 1:15, 90:1 to 1:10, 90:1 to 1:5, 90:1 to 1:4, 90:1 to 1:3, 90:1 to 1:2, 85:1 to 1:85, 85:1 to 1:95, 85:1 to 1:90, 85:1 to 1:80, 85:1 to 1:75, 85:1 to 1:70, 85:1 to 1:65, 85:1 to 1:60, 85:1 to 1:55, 85:1 to 1:50, 85:1 to 1:45, 85:1 to 1:40, 85:1 to 1:35, 85:1 to 1:30, 85:1 to 1:25, 85:1 to 1:20, 85:1 to 1:15, 85:1 to 1:10, 85:1 to 1:5, 85:1 to 1:4, 85:1 to 1:3, 85:1 to 1:2, 80:1 to 1:80, 80:1 to 1:95, 80:1 to 1:90, 80:1 to 1:85, 80:1 to 1:75, 80:1 to 1:70, 80:1 to 1:65, 80:1 to 1:60, 80:1 to 1:55, 80:1 to 1:50, 80:1 to 1:45, 80:1 to 1:40, 80:1 to 1:35, 80:1 to 1:30, 80:1 to 1:25, 80:1 to 1:20, 80:1 to 1:15, 80:1 to 1:10, 80:1 to 1:5, 80:1 to 1:4, 80:1 to 1:3, 80:1 to 1:2, 75:1 to 1:75, 75:1 to 1:95, 75:1 to 1:90, 75:1 to 1:85, 75:1 to 1:80, 75:1 to 1:70, 75:1 to 1:65, 75:1 to 1:60, 75:1 to 1:55, 75:1 to 1:50, 75:1 to 1:45, 75:1 to 1:40, 75:1 to 1:35, 75:1 to 1:30, 75:1 to 1:25, 75:1 to 1:20, 75:1 to 1:15, 75:1 to 1:10, 75:1 to 1:5, 75:1 to 1:4, 75:1 to 1:3, 75:1 to 1:2, 70:1 to 1:70, 70:1 to 1:95, 70:1 to 1:90, 70:1 to 1:85, 70:1 to 1:80, 70:1 to 1:75, 70:1 to 1:65, 70:1 to 1:60, 70:1 to 1:55, 70:1 to 1:50, 70:1 to 1:45, 70:1 to 1:40, 70:1 to 1:35, 70:1 to 1:30, 70:1 to 1:25, 70:1 to 1:20, 70:1 to 1:15, 70:1 to 1:10, 70:1 to 1:5, 70:1 to 1:4, 70:1 to 1:3, 70:1 to 1:2, 65:1 to 1:65, 65:1 to 1:95, 65:1 to 1:90, 65:1 to 1:85, 65:1 to 1:80, 65:1 to 1:75, 65:1 to 1:70, 65:1 to 1:60, 65:1 to 1:55, 65:1 to 1:50, 65:1 to 1:45, 65:1 to 1:40, 65:1 to 1:35, 65:1 to 1:30, 65:1 to 1:25, 65:1 to 1:20, 65:1 to 1:15, 65:1 to 1:10, 65:1 to 1:5, 65:1 to 1:4, 65:1 to 1:3, 65:1 to 1:2, 60:1 to 1:60, 60:1 to 1:95, 60:1 to 1:90, 60:1 to 1:85, 60:1 to 1:80, 60:1 to 1:75, 60:1 to 1:70, 60:1 to 1:65, 60:1 to 1:55, 60:1 to 1:50, 60:1 to 1:45, 60:1 to 1:40, 60:1 to 1:35, 60:1 to 1:30, 60:1 to 1:25, 60:1 to 1:20, 60:1 to 1:15, 60:1 to 1:10, 60:1 to 1:5, 60:1 to 1:4, 60:1 to 1:3, 60:1 to 1:2, 55:1 to 1:55, 55:1 to 1:95, 55:1 to 1:90, 55:1 to 1:85, 55:1 to 1:80, 55:1 to 1:75, 55:1 to 1:70, 55:1 to 1:65, 55:1 to 1:60, 55:1 to 1:50, 55:1 to 1:45, 55:1 to 1:40, 55:1 to 1:35, 55:1 to 1:30, 55:1 to 1:25, 55:1 to 1:20, 55:1 to 1:15, 55:1 to 1:10, 55:1 to 1:5, 55:1 to 1:4, 55:1 to 1:3, 55:1 to 1:2, 50:1 to 1:95, 50:1 to 1:90, 50:1 to 1:85, 50:1 to 1:80, 50:1 to 1:75, 50:1 to 1:70, 50:1 to 1:65, 50:1 to 1:60, 50:1 to 1:55, 50:1 to 1:45, 50:1 to 1:40, 50:1 to 1:35, 50:1 to 1:30, 50:1 to 1:25, 50:1 to 1:20, 50:1 to 1:15, 50:1 to 1:10, 50:1 to 1:5, 50:1 to 1:4, 50:1 to 1:3, 50:1 to 1:2, 45:1 to 1:45, 45:1 to 1:95, 45:1 to 1:90, 45:1 to 1:85, 45:1 to 1:80, 45:1 to 1:75, 45:1 to 1:70, 45:1 to 1:65, 45:1 to 1:60, 45:1 to 1:55, 45:1 to 1:50, 45:1 to 1:40, 45:1 to 1:35, 45:1 to 1:30, 45:1 to 1:25, 45:1 to 1:20, 45:1 to 1:15, 45:1 to 1:10, 45:1 to 1:5, 45:1 to 1:4, 45:1 to 1:3, 45:1 to 1:2, 40:1 to 1:40, 40:1 to 1:95, 40:1 to 1:90, 40:1 to 1:85, 40:1 to 1:80, 40:1 to 1:75, 40:1 to 1:70, 40:1 to 1:65, 40:1 to 1:60, 40:1 to 1:55, 40:1 to 1:50, 40:1 to 1:45, 40:1 to 1:35, 40:1 to 1:30, 40:1 to 1:25, 40:1 to 1:20, 40:1 to 1:15, 40:1 to 1:10, 40:1 to 1:5, 40:1 to 1:4, 40:1 to 1:3, 40:1 to 1:2, 35:1 to 1:35, 35:1 to 1:95, 35:1 to 1:90, 35:1 to 1:85, 35:1 to 1:80, 35:1 to 1:75, 35:1 to 1:70, 35:1 to 1:65, 35:1 to 1:60, 35:1 to 1:55, 35:1 to 1:50, 35:1 to 1:45, 35:1 to 1:40, 35:1 to 1:30, 35:1 to 1:25, 35:1 to 1:20, 35:1 to 1:15, 35:1 to 1:10, 35:1 to 1:5, 35:1 to 1:4, 35:1 to 1:3, 35:1 to 1:2, 30:1 to 1:30, 30:1 to 1:95, 30:1 to 1:90, 30:1 to 1:85, 30:1 to 1:80, 30:1 to 1:75, 30:1 to 1:70, 30:1 to 1:65, 30:1 to 1:60, 30:1 to 1:55, 30:1 to 1:50, 30:1 to 1:45, 30:1 to 1:40, 30:1 to 1:35, 30:1 to 1:25, 30:1 to 1:20, 30:1 to 1:15, 30:1 to 1:10, 30:1 to 1:5, 30:1 to 1:4, 30:1 to 1:3, 30:1 to 1:2, 25:1 to 1:25, 25:1 to 1:95, 25:1 to 1:90, 25:1 to 1:85, 25:1 to 1:80, 25:1 to 1:75, 25:1 to 1:70, 25:1 to 1:65, 25:1 to 1:60, 25:1 to 1:55, 25:1 to 1:50, 25:1 to 1:45, 25:1 to 1:40, 25:1 to 1:35, 25:1 to 1:30, 25:1 to 1:20, 25:1 to 1:15, 25:1 to 1:10, 25:1 to 1:5, 25:1 to 1:4, 25:1 to 1:3, 25:1 to 1:2, 20:1 to 1:95, 20:1 to 1:90, 20:1 to 1:85, 20:1 to 1:80, 20:1 to 1:75, 20:1 to 1:70, 20:1 to 1:65, 20:1 to 1:60, 20:1 to 1:55, 20:1 to 1:50, 20:1 to 1:45, 20:1 to 1:40, 20:1 to 1:35, 20:1 to 1:30, 20:1 to 1:25, 20:1 to 1:15, 20:1 to 1:10, 20:1 to 1:5, 20:1 to 1:4, 20:1 to 1:3, 20:1 to 1:2, 15:1 to 1:15, 15:1 to 1:95, 15:1 to 1:90, 15:1 to 1:85, 15:1 to 1:80, 15:1 to 1:75, 15:1 to 1:70, 15:1 to 1:65, 15:1 to 1:60, 15:1 to 1:55, 15:1 to 1:50, 15:1 to 1:45, 15:1 to 1:40, 15:1 to 1:35, 15:1 to 1:30, 15:1 to 1:25, 15:1 to 1:20, 15:1 to 1:10, 15:1 to 1:5, 15:1 to 1:4, 15:1 to 1:3, 15:1 to 1:2, 10:1 to 1:10, 10:1 to 1:95, 10:1 to 1:90, 10:1 to 1:85, 10:1 to 1:80, 10:1 to 1:75, 10:1 to 1:70, 10:1 to 1:65, 10:1 to 1:60, 10:1 to 1:55, 10:1 to 1:50, 10:1 to 1:45, 10:1 to 1:40, 10:1 to 1:35, 10:1 to 1:30, 10:1 to 1:25, 10:1 to 1:20, 10:1 to 1:15, 10:1 to 1:5, 10:1 to 1:4, 10:1 to 1:3, 10:1 to 1:2, 5:1 to 1:5, 5:1 to 1:95, 5:1 to 1:90, 5:1 to 1:85, 5:1 to 1:80, 5:1 to 1:75, 5:1 to 1:70, 5:1 to 1:65, 5:1 to 1:60, 5:1 to 1:55, 5:1 to 1:50, 5:1 to 1:45, 5:1 to 1:40, 5:1 to 1:35, 5:1 to 1:30, 5:1 to 1:25, 5:1 to 1:20, 5:1 to 1:15, 5:1 to 1:10, 5:1 to 1:4, 5:1 to 1:3, 5:1 to 1:2, 4:1 to 1:4, 4:1 to 1:95, 4:1 to 1:90, 4:1 to 1:85, 4:1 to 1:80, 4:1 to 1:75, 4:1 to 1:70, 4:1 to 1:65, 4:1 to 1:60, 4:1 to 1:55, 4:1 to 1:50, 4:1 to 1:45, 4:1 to 1:40, 4:1 to 1:35, 4:1 to 1:30, 4:1 to 1:25, 4:1 to 1:20, 4:1 to 1:15, 4:1 to 1:10, 4:1 to 1:5, 4:1 to 1:3, 4:1 to 1:2, 3:1 to 1:3, 3:1 to 1:95, 3:1 to 1:90, 3:1 to 1:85, 3:1 to 1:80, 3:1 to 1:75, 3:1 to 1:70, 3:1 to 1:65, 3:1 to 1:60, 3:1 to 1:55, 3:1 to 1:50, 3:1 to 1:45, 3:1 to 1:40, 3:1 to 1:35, 3:1 to 1:30, 3:1 to 1:25, 3:1 to 1:20, 3:1 to 1:15, 3:1 to 1:10, 3:1 to 1:5, 3:1 to 1:4, 3:1 to 1:2, 2:1 to 1:2, 2:1 to 1:95, 2:1 to 1:90, 2:1 to 1:85, 2:1 to 1:80, 2:1 to1:75, 2:1 to 1:70, 2:1 to 1:65, 2:1 to 1:60, 2:1 to 1:55, 2:1 to 1:50, 2:1 to 1:45, 2:1 to 1:40, 2:1 to 1:35, 2:1 to 1:30, 2:1 to 1:25, 2:1 to 1:20, 2:1 to 1:15, 2:1 to 1:10, 2:1 to 1:5, 2:1 to 1:4, 2:1 to 1:3.

The compounds of the formula (I) or the active compounds from the class of the chitin synthesis inhibitors, the molting hormone agonists or other classes with at least one basic centre are capable of forming, for example, acid addition salts, for example with strong inorganic acids such as mineral acids, for example perchloric acid, sulphuric acid, nitric acid, nitrous acid, a phosphorus acid or a hydrohalic acid, with strong organic carboxylic acids such as unsubstituted or substituted, for example halogen-substituted, $C_1$-$C_4$-alkanecarboxylic acids, for example acetic acid, saturated or unsaturated dicarboxylic acids, for example oxalic acid, malonic acid, succinic acid, maleic acid, fumaric acid and phthalic acid, hydroxycarboxylic acids, for example ascorbic acid, lactic acid, malic acid, tartaric acid and citric acid, or benzoic acid, or with organic sulphonic acids such as unsubstituted or substituted, for example halogen-substituted, $C_1$-$C_4$-alkane or arylsulphonic acids, for example methane or p-toluenesulphonic acid. The compounds of the formula (1) or the active compounds from the class of the chitin synthesis inhibitors, the molting hormone agonists or other classes with at least one acidic group are capable of forming, for example, salts with bases, for example metal salts, such as alkali or alkaline-earth metal salts, for example sodium, potassium or magnesium salts, or salts with ammonia or an organic amine such as morpholine, piperidine, pyrrolidine, a lower mono, di or trialkylamine, for example, ethyl, diethyl, triethyl or dimethylpropylamine, or a lower mono, di or trihydroxyalkylamine, for example mono, di or triethanolamine. Moreover, if appropriate, it may also be possible for corresponding internal salts to be formed. In the context of the invention, agrochemically advantageous salts are preferred. With a view to the close relationship between the compounds of the formula (I) or the active compounds from the class of the chitin synthesis inhibitors, the molting hormone agonists or other classes in free form and in the form of their salts, each reference above and below to the free compounds of the formula (I) or to free active compounds from the class of the chitin synthesis inhibitors, the molting hormone agonists or other classes or to their salts is meant to be understood such that this also includes the corresponding salts and the free compounds of the formula (I) or the free active compounds from the class of the chitin synthesis inhibitors, the molting hormone agonists or other classes, respectively, if this is applicable and expedient. This also applies in a corresponding manner to tautomers of the compounds of the formula (I) and the active compounds from the class of the chitin synthesis inhibitors, the molting hormone agonists or other classes and to their salts.

In the context of the present invention, the term "active compound combination" refers to various combinations of compounds of the formula (I) and active compounds from the class of the chitin synthesis inhibitors, the molting hormone agonists or other classes, for example in the form of a single ready-mix, in a combined spray mixture composed of separate formulations of the individual active compounds, for example a tank-mix or in a combined use of the individual active compounds in the case of their sequential application, for example in succession within an appropriate short period of time of, for example, a few hours or days. According to a preferred embodiment, the order of the application of the compounds of the formula (I) and the active compounds from the class of the chitin synthesis inhibitors, the molting hormone agonists or other classes is not critical for the practice of the present invention.

When using the active compound combinations according to the invention as insecticides and acaricides, the application rates can be varied within a relatively wide range, depending on the kind of application. The application rate of the active compound combinations according to the invention is when treating plant parts, e.g. leaves: from 0.1 to 10,000 g/ha, preferably from 10 to 1,000 g/ha, particularly preferably from 50 to 300 g/ha (when the application is carried out by watering or dripping, it may even be possible to reduce the application rate, in particular when inert substrates such as rock wool or perlite are used); when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed; when treating the soil: from 0.1 to 10,000 g/ha, preferably from 1 to 5,000 g/ha.

These application rates are mentioned only by way of example and are not limiting in the sense of the invention.

The active compound combinations according to the invention can be employed for protecting plants for a certain period of time after treatment against attack by the animal pests mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

The active compound combinations according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can preferably be used as crop protection compositions. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretas* spp., *Agelastica alni, Agriotes* spp., *Amphimallon solstitialis, Anobium punctatum, Anoplophora* spp., *Anthonomus* spp., *Anthrenus* spp, *Apogonia* spp., *Atomaria* spp., *Attagenus* spp, *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp, *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops farcatus, Diconocoris hewetti, Dysdercus* spp., *Euschistas* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare*, *Oniscus asellus* and *Porcellio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., spp., *Hofmannophila pseudospretella*, *Homona magnanima*, *Hyponomeuta padella*, *Laphygma* spp., *Leuoptera* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phylloenistis citrella*, *Pieris* spp., *Plutella xylostella*, *Prodenia* spp., *Pseudaletia* spp., *Pseudoplusia includens*, *Pyrausta nubilalis*, *Rachiplusia* spp. *Spodoptera* spp., *Thermesia gemmatalis*, *Tinea pellionella*, *Tineola bisselliella*, *Tortrix viridana*, *Trichoplusia* spp., *Tuta* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biforniis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharine*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans* and *Xiphinema* spp.

If appropriate, the active compound combinations according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms).

The active compounds can be converted into the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active compound, synthetic substances impregnated with active compound, fertilizers and also microencapsulations in polymeric substances.

These formulations are produced in a known manner, for example by mixing the active compounds with extenders, i.e. liquid solvents, and/or solid carriers, optionally with the use of surfactants, i.e. emulsifiers and/or dispersants, and/or foam formers. The formulations are produced either in suitable plants or else before or during application.

Suitable for use as auxiliaries are substances which are suitable for imparting to the composition itself and/or to preparations derived therefrom (for example spray liquors, seed dressings) particular properties such as certain technical properties and/or also particular biological properties. Typical auxiliaries include: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

According to the invention, a carrier is a natural or synthetic, organic or inorganic substance which may be solid or liquid and with which the active compounds are mixed or bonded for better applicability, in particular for application to plants or plant parts or seed. The solid or liquid carrier is generally inert and should be suitable for use in agriculture.

Suitable solid or liquid carriers are:

for example ammonium salts and natural rock flours, such as kaolins, clays, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam-formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Furthermore, suitable oligomers or polymers, for example those derived from vinylic monomers, from acrylic acid, from EO land/or PO alone or in combination with, for example, (poly)alcohols or (poly)amines. It is also possible to use lignin and its sulphonic acid derivatives, unmodified and modified celluloses, aromatic and/or aliphatic sulphonic acids and also their adducts with formaldehyde.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

Other possible additives are perfumes, mineral or vegetable oils which are optionally modified, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability, may also be present.

The active compound content of the use forms prepared from the commercially available formulations may vary within wide limits. The active compound concentration of the use forms is in the range of from 0.00000001 to 97% by weight of active compound, preferably in the range of from 0.0000001 to 97% by weight, particularly preferably in the range of from 0.000001 to 83% by weight or 0.000001 to 5% by weight, and very particularly preferably in the range of from 0.0001 to 1% by weight.

The active compound combinations according to the invention can be present in their commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

When used as insecticides, the active compound combinations according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The compounds are employed in a customary manner appropriate for the use forms.

All plants and plant parts can be treated in accordance with the invention. Plants are understood here to mean all plants and plant populations, such as desired and undesired wild plants or crop plants (including naturally occurring crop plants). Crop plants can thus be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. The plant parts also include harvested material and also vegetative and generative propagation material, for example fruits, seeds, cuttings, tubers, rhizomes, slips, seed, bulbils, layers and runners.

Treatment according to the invention of the plants and plant parts with the active compound combinations is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

The following plants may be mentioned as plants which can be treated according to the invention: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leeks, onions), Papilionaceae sp. (for example peas); major crop plants such as Gramineae sp. (for example maize, turf, cereals such as wheat, rye, rice, barley, oats, millet and triticale), Asteraceae sp. (for example sunflower), Brassicaceae sp. (for example white cabbage, red cabbage, broccoli, cauliflower, Brussels sprouts, pak choi, kohlrabi, small radishes, and also oilseed rape, mustard, horseradish and cress), Fabacae sp. (for example beans, peanuts), Papilionaceae sp. (for example soya bean), Solanaceae sp. (for example potatoes), Chenopodiaceae sp. (for example sugar beet, fodder beet, Swiss chard, beetroot); useful plants and ornamental plants in gardens and forests; and in each case genetically modified types of these plants.

The active compound combinations according to the invention are particularly suitable for the treatment of seed. Here, particular mention may be made of the combinations according to the invention mentioned above as preferred or particularly preferred. Thus, most of the damage to crop plants which is caused by pests occurs as early as when the seed is infested during storage and after the seed is introduced into the soil, and during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection products after sowing or after emergence of the plants. It is furthermore desirable to optimize the amount of active compound employed in such a way as to provide optimum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and also of the germinating plant with a minimum of crop protection products being employed.

Accordingly, the present invention also relates in particular to a method for protecting seed and germinating plants against attack by pests by treating the seed with an active compound combination according to the invention. The method according to the invention for protecting seed and germinating plants against attack by pests comprises a method where the seed is treated simultaneously with an active compound of the formula (I) and one of the active compounds 1 to 22 listed individually above from the class of the chitin synthesis inhibitors, the molting hormone agonists or other classes. It also comprises a method where the seed is treated at different times with an active compound of the formula (I) and one of the active compounds 1 to 22 listed individually above from the class of the chitin synthesis inhibitors, the molting hormone agonists or other classes. The invention also relates to the use of the active compound combinations according to the invention for treating seed for protecting the seed and the resulting plant against pests. Furthermore, the invention relates to seed treated with an active compound combination according to the invention for protection against pests. The invention also relates to seed treated simultaneously with an active compound of the formula (I) and one of the active compounds 1 to 22 listed individually above from the class of the chitin synthesis inhibitors, the molting hormone agonists or other classes. The invention furthermore relates to seed treated at different times with an active compound of the formula (I) and one of the active compounds 1 to 22 listed individually above from the class of the chitin synthesis inhibitors, the molting hormone agonists or other classes. In the case of seed treated at different times with an active compound of the formula (I) and one of the active compounds 1 to 22 listed individually above from the class of the chitin synthesis inhibitors, the molting hormone agonists or other classes, the individual active compounds of the compostion according to the invention may be present in different layers on the seed. The layers comprising an active compound of the formula (I) and one of the active compounds 1 to 22 listed individually above from the class of the chitin synthesis inhibitors, the molting hormone agonists or other classes may optionally be separated by an intermediate layer. The invention also relates to seed where an active compound of the formula (I) and one of the active compounds 1 to 22 listed individually above from the class of the chitin synthesis inhibitors, the molting hormone agonists or other classes are applied as component of a coating or as a further layer or further layers in addition to a coating.

One of the advantages of the present invention is that, because of the particular systemic properties of the active compound combinations according to the invention, treatment of the seed with these compositions not only protects the seed itself, but also the resulting plants after emergence, from pests. In this manner, the immediate treatment of the crop at the time of sowing or shortly thereafter can be dispensed with.

A farther advantage is the synergistically increased insecticidal activity of the active compound combinations according to the invention in comparison with the individual insecticidally active compound, which exceeds the expected activity of the two active compounds when applied individually. Also advantageous is the synergictic enhancement of the fungicidal activity of the active compound combinations according to the invention compared with the individual fungicidally active compound, which exceeds the expected activity of the active compound applied individually. This makes possible an optimization of the amount of active compounds employed.

It is likewise to be considered advantageous that the active compound combinations according to the invention can be used in particular also for transgenic seed, where the plants arising from this seed are capable of expressing a protein targeted at pests. By treating such seed with the active compound combinations according to the invention, certain pests can already be controlled by the expression of the for example insecticidal protein and in addition can be protected from damage by the active compound combinations according to the invention.

The active compound combinations according to the invention are suitable for protecting seed of any plant variety as already mentioned above which is employed in agriculture, in the greenhouse, in forests or in horticulture. In particular, this takes the form of seed of maize, peanut, canola, oilseed rape, poppy, soya beans, cotton, beet (for example sugar beet and fodder beet), rice, millet, wheat, barley, oats, rye, sunflower, tobacco, potatoes or vegetables (for example tomatoes, cabbage species). The active compound combinations according to the invention are likewise suitable for treating the seed of fruit plants and vegetables as already mentioned above. The treatment of the seed of maize, soya beans, cotton, wheat and canola or oilseed rape is of particular importance.

As already mentioned above, the treatment of transgenic seed with an active compound combination according to the invention is likewise of particular importance. This is the seed of plants which generally comprise at least one heterologous gene which controls the expression of a polypeptide having particular insecticidal properties. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for the treatment of transgenic seed comprising at least one heterologous gene which originates from *Bacillus* sp. and whose gene product shows activity against the European corn borer and/or the Western corn rootworm. Particularly preferably, this is a heterologous gene which originates from *Bacillus thuringiensis*.

Within the context of the present invention, the active compound combination according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits.

When treating the seed, care must generally be taken that the amount of the active compound combination according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples include the dyes known by the names Rhodamine B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants.

Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/fonnaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are know (cf. R. Wegler "Chemie der Pflanzenschutz- and Schädlingsbekämpfungsmittel" [Chemistry of the Crop Protection Compositions and Pesticides], vol. 2, Springer Verlag, 1970, pp. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. For example, the following effects exceeding the effects actually to be expected are possible: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processibility of the harvested products.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are understood as meaning phytopathogenic fungi, bacteria and viruses. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid vigour, which results in generally higher yield, increased vigour, better health and better resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar (e.g. WO 1991/002069).

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an Eleusine EPSPS (WO 2001/66704). It can also be a mutated EPSPS, as described, for example, in EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyltransferase enzyme as described, for example, in WO 2002/036782, WO 2003/092360, WO 2005/012515 and WO 2007/024782. Glyphosate-tolerant plants can also be obtained by selecting plants containing naturally occurring mutations of the abovementioned genes as described, for example, in WO 2001/024615 or WO 2003/013226.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from Streptomyces species for example). Plants expressing an exogenous phosphinothricin acetyltransferase have been described, for example, in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme according to WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides, as described, for example, in Tranel and Wright, Weed Science (2002), 50, 700-712, and also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants has been described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and also in the international publication WO 1996/033270. Further imidazolinone-tolerant plants have also been described, for example in WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding, as described, for example, for soya beans in U.S. Pat. No. 5,084,081 for rice in WO 1997/41218, for sugar beet in U.S. Pat. No. 5,773,702 and WO 1999/057965, for lettuce in U.S. Pat. No. 5,198,599 or for sunflower in WO 2001/065922.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins compiled by Crickmore et al., Microbiology and Molecular Biology Reviews (1998), 62, 807-813, updated by Crickmore et al. (2005) in the *Bacillus thuringiensis* toxin nomenclature, (online at: http://www.lifesci.sussex.ac.uk/Home/Neil_Crickmore/Bt/), or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect, species affected, and/or because of changes induced in the encoding DNA during cloning or transformation, such as the Cry3Bb1 protein in maize events MON863 or MON88017, or the Cry3A protein in maize event MIR604; or 5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants, as described in WO 2000/004173 or EP 04077984.5 or EP 06009836.5.

b. plants which contain a stress tolerance-enhancing transgene capable of reducing the expression and/or the activity of the PARG encoding genes of the plants or plant cells, as described, for example, in WO 2004/090140;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, for example, in EP 04077624.7 or WO 2006/133827 or PCT/EP07/002433.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications. These transgenic plants synthesizing a modified starch are described, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 and WO 1997/20936.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, as described in EP 0663956, WO 1996/001904, WO 1996/021023, WO 1998/039460 and WO 1999/024593, plants which produce alpha-1,4-glucans, as described in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants which produce alpha-1,6-branched alpha-1,4-glucans, as described in WO 2000/73422, and plants which produce alternan, as described in WO 2000/047727, EP 06077301.7, U.S. Pat. No. 5,908,975 and EP 0728213.

3) Transgenic plants which produce hyaluronan, as described, for example, in WO 2006/032538, WO 2007/039314, WO 2007/039315, WO 2007/039316, JP 2006/304779 and WO 2005/012529.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes, as described in WO 1998/000549;

b) plants, such as cotton plants, which contain an altered form of rsw2 or rsw3 homologous nucleic acids, as described in WO 2004/053219;

c) plants, such as cotton plants, with increased expression of sucrose phosphate synthase as described in WO 2001/017333;

d) plants, such as cotton plants, with an increased expression of sucrose synthase, as described in WO 02/45485;

e) plants, such as cotton plants, wherein the timing of the plasmodesmatal gating at the basis of the fibre cell is altered, for example through downregulation of fibre-selective β-1,3-glucanase as described in WO 2005/017157;

f) plants, such as cotton plants, which have fibres with altered reactivity, for example through the expression of the N-acetylglucosaminetransferase gene including nodC and chitin synthase genes, as described in WO 2006/136351.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content, as described, for example, in U.S. Pat. No. 5,969,169, U.S. Pat. No. 5,840,946 or U.S. Pat. No. 6,323,392 or U.S. Pat. No. 6,063,947;

b) plants, such as oilseed rape plants, which produce oil having a low linolenic acid content, as described in U.S. Pat. No. 6,270,828, U.S. Pat. No. 6,169,190 or U.S. Pat. No. 5,965,755;

c) plants, such as oilseed rape plants, which produce oil having a low level of saturated fatty acids, as described, for example, in U.S. Pat. No. 5,434,283.

Particularly useful transgenic plants which may be treated according to the invention are plants which comprise one or more genes which encode one or more toxins and are the transgenic plants available under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

The plants listed can be treated in a particularly advantageous manner with the active compound combinations according to the invention. The preferred ranges stated above for the active compound combinations also apply to the treatment of these plants. Particular emphasis is given to the treatment of plants with the active compound combinations specifically mentioned in the present text.

The active compound combinations according to the invention are not only active against plant pests, hygiene pests and stored-product pests, but also, in the veterinary medicine sector, against animal parasites (ectoparasites and endoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* app., *Werneckiella* spp., *Lepikentron* app., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. The control of these arthropods is intended to reduce cases of death and reduced productivity (of meat, milk, wool, hides, eggs, honey etc.), and so more economic and easier animal husbandry is possible by use of the active compound combinations according to the invention.

The active compound combinations according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intaperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compound combinations according to the invention show a potent insecticidal action against insects which destroy industrial materials.

Preferred but nonlimiting examples include the following insects:

beetles, such as *Hylotrupes bajulus, Chlorophorus pilosis, Anobium punctatum, Xestobium rufovillosum, Ptilinus pecticornis, Dendrobium pertinex, Emobius mollis, Priobium earpini, Lyctus brunneus, Lyctus africanus, Lyctus planicoliis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur*;

termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*;

bristletails, such as *Lepisma saccarina*.

Industrial materials in the present connection are understood to mean inanimate materials, such as preferably plastics, adhesives, sizes, papers and cards, leather, wood, processed wood products and coating compositions.

The ready-to-use compositions may optionally also comprise further insecticides, and optionally one or more fungicides.

With respect to possible addition partners for mixing, reference is made to the insecticides and fungicides mentioned above.

Moreover, the active compound combinations according to the invention can be employed for protecting objects which come into contact with saltwater or brackish water, in particular hulls, screens, nets, buildings, moorings and signalling systems, against fouling.

Furthermore, the active compound combinations according to the invention can be used alone or in combination with other active compounds as antifouling compositions.

The active compound combinations are also suitable for controlling animal pests in domestic, hygiene and stored-product protection, in particular insects, arachnids and mites, which are encountered in enclosed spaces, for example dwellings, factory halls, offices, vehicle cabins and the like. They can be used alone or in combination with other active compounds and auxiliaries in domestic insecticide products for controlling these pests. They are effective against sensitive and resistant species, and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp, *Phylloera vestratrix, Phthirus pubis*.

From the order of the Heteroptera, for example, *Cimex hemipterus, Cimex lectularius, Rhodinus prolixus, Triatoma infestans*.

The use in the field of domestic insecticides takes place alone or in combination with other suitable active compounds such as phosphoric esters, carbamates, neonicotinoids, pyrethroids, growth regulators or active compounds from other known insecticide classes.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The good insecticidal and acaricidal action of the active compound combinations according to the invention can be seen from the examples which follow. While the individual active compounds show weaknesses in the action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated according to S. R. Colby, Weeds 15 (1967), 20-22, as follows:

If

X is the kill rate, expressed in % of the untreated control, when the active compound A is used at an application rate of m g/ha or in a concentration of m ppm, Y is the kill rate, expressed in % of the untreated control, when the active compound B is used at an application rate of n g/ha or in a concentration of n ppm, E is the kill rate, expressed in % of the untreated control, when the active compounds A and B are used at application rates of m and n g/ha or in a concentration of m and n ppm, then $$E = X + Y - \frac{X \times Y}{100}$$

If the actual insecticidal or acaricidal kill rate exceeds the calculated value, the kill of the combination is superadditive, i.e. a synergistic effect is present. In this case, the actually observed kill rate must exceed the value calculated using the above formula for the expected kill rate (E).

EXAMPLES

Example A

*Myzus persicae* Test

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by spraying with the active compound preparation of the desired concentration.

After the desired period of time, the kill in % is determined. 100% means that all of the aphids have been killed; 0% means that none of the aphids have been killed. The kill rates determined are entered into Colby's formula (see above).

In this test, for example, the following active compound combinations in accordance with the present application show a synergistically enhanced activity compared to the active compounds applied individually:

TABLE A

*Myzus persicae* test

| Active compound | Concentration in g/ha | Kill in % after $1^d$ | |
|---|---|---|---|
| compound (I-4) | 4 | 30 | |
| flufenoxuron | 4 | 0 | |
| lufenuron | 4 | 0 | |
| methoxyfenozide | 4 | 0 | |
| triflumuron | 4 | 0 | |
| | | found* | calc.** |
| compound (I-4) + flufenoxuron (1:1) according to the invention | 4 + 4 | 80 | 30 |
| compound (I-4) + lufenuron (1:1) according to the invention | 4 + 4 | 80 | 30 |
| | | found | calc.** |
| compound (I-4) + methoxyfenozide (1:1) according to the invention | 4 + 4 | 70 | 30 |
| compound (I-4) + triflumuron (1:1) according to the invention | 4 + 4 | 80 | 30 |
| compound (I-6) | 0.8 | 70 | |

TABLE A-continued

*Myzus persicae* test

| Active compound | Concentration in g/ha | Kill in % after $1^d$ | |
|---|---|---|---|
| flufenoxuron | 0.8 | 0 | |
| triflumuron | 0.8 | 0 | |
| | | found* | calc.** |
| compound (I-6) + flufenoxuron (1:1) according to the invention | 0.8 + 0.8 | 100 | 70 |
| compound (I-6) + Triflumuron (1:1) according to the invention | 0.8 + 0.8 | 90 | 70 |

*found = activity found
**calc. = activity calculated using Colby's formula

Example B

*Phaedon cochleariae* Larvae Test

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by spraying with the active ingredient formulation of the desired concentration and populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The kill rates determined are entered into Colby's formula (see above).

In this test, the following active compound combination in accordance with the present application showed a synergistically enhanced activity compared to the active compounds applied individually:

TABLE B

*Phaedon cochleariae* larvae test

| Active compound | Concentration in g/ha | Kill in % after $2^d$ | |
|---|---|---|---|
| compound (I-6) | 100 | 0 | |
| flufenoxuron | 100 | 0 | |
| | | found* | calc.** |
| compound (I-6) + flufenoxuron (1:1) according to the invention | 100 + 100 | 17 | 0 |
| compound (I-6) | 100 | 0 | |
| compound (I-4) | 100 | 0 | |
| | 4 | 0 | |
| compound (I-5) | 100 | 0 | |
| | 4 | 0 | |
| lufenuron | 100 | 17 | |
| triflumuron | 4 | 0 | |
| | | found* | calc.** |
| compound (I-6) + lufenuron (1:1) according to the invention | 100 + 100 | 33 | 17 |

TABLE B-continued

Phaedon cochleariae larvae test

| Active compound | Concentration in g/ha | Kill in % after $2^d$ | |
|---|---|---|---|
| compound (I-4) + lufenuron (1:1) according to the invention | 100 + 100 | 50 | 17 |
| compound (I-5) + lufenuron (1:1) according to the invention | 100 + 100 | 33 | 17 |
| compound (I-4) + triflumuron (1:1) according to the invention | 4 + 4 | 17 | 0 |
| compound (I-5) + triflumuron (1:1) according to the invention | 4 + 4 | 17 | 0 |

*found = activity found
**calc. = activity calculated using Colby's formula

Example C

Spodoptera frugiperda Larvae Test

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (Brassica oleracea) are treated by being sprayed with the preparation of active compound of the desired concentration and are populated with larvae of the armyworm (Spodoptera frugiperda) while the leaves are still moist.

After the desired period of time, the kill in % is determined. 100% means that all caterpillars have been killed; 0% means that none of the caterpillars have been killed. The kill rates determined are entered into Colby's formula (see above).

In this test the following active compound combinations in accordance with the present application show a synergistically enhanced activity compared to the active compounds applied individually:

TABLE C

Spodoptera frugiperda test

| Active compound | Concentration in g/ha | Kill in % after $2^d$ | |
|---|---|---|---|
| compound (I-6) | 0.8 | 0 | |
| triflumuron | 0.8 | 33 | |
| | | found* | calc.** |
| compound (I-6) + triflumuron (1:1) according to the invention | 0.8 + 0.8 | 50 | 33 |
| compound (I-6) | 20 | 0 | |
| | 0.8 | 0 | |
| compound (I-4) | 20 | 0 | |
| | 0.8 | 0 | |
| | 0.16 | 0 | |
| compound (I-5) | 4 | 0 | |
| | 0.8 | 0 | |

TABLE C-continued

Spodoptera frugiperda test

| Active compound | Concentration in g/ha | Kill in % after $2^d$ | |
|---|---|---|---|
| flufenoxuron | 0.8 | 33 | |
| methoxyfenozide | 20 | 83 | |
| | 4 | 33 | |
| triflumuron | 0.16 | 50 | |
| | | found* | calc.** |
| compound (I-6) + flufenoxuron (1:1) according to the invention | 0.8 + 0.8 | 67 | 33 |
| compound (I-4) + flufenoxuron (1:1) according to the invention | 0.8 + 0.8 | 67 | 33 |
| compound (I-5) + flufenoxuron (1:1) according to the invention | 0.8 + 0.8 | 83 | 33 |
| compound (I-6) + methoxyfenozide (1:1) according to the invention | 20 + 20 | 100 | 83 |
| compound (I-4) + methoxyfenozide (1:1) according to the invention | 20 + 20 | 100 | 83 |
| compound (I-5) + methoxyfenozide (1:1) according to the invention | 4 + 4 | 83 | 33 |
| compound (I-4) + triflumuron (1:1) according to the invention | 0.16 + 0.16 | 67 | 50 |

*found = activity found
**calc. = activity calculated using Colby's formula

Example D

Tetranychus urticae Test (OP-Resistant/Spray Treatment)

Solvents: 78 parts by weight of acetone 1.5 parts by weight of dimethylformamide Emulsifier: 0.5 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Discs of bean leaves (Phaseolus vulgaris) which are infested by all stages of the greenhouse red spider mite (Tetranychus urticae) are sprayed with an active compound preparation of the desired concentration.

After the desired period of time, the effect in % is determined. 100% means that all of the spider mites have been killed; 0% means that none of the spider mites have been killed.

In this test, the following active compound combination in accordance with the present application showed a synergistically enhanced activity compared to the active compounds applied individually:

TABLE D-1

Tetranychus urticae test

| Active compound | Concentration in g/ha | Kill in % after $6^d$ |
|---|---|---|
| compound (I-4) | 20 | 0 |
| compound (I-5) | 100 | 0 |
| | 20 | 0 |

TABLE D-1-continued

Tetranychus urticae test

| Active compound | Concentration in g/ha | Kill in % after 6$^d$ | |
|---|---|---|---|
| | | found* | calc.** |
| flufenoxuron | 20 | 0 | |
| methoxyfenozide | 100 | 0 | |
| compound (I-4) + flufenoxuron (1:1) according to the invention | 20 + 20 | 90 | 0 |
| compound (I-5) + flufenoxuron (1:1) according to the invention | 20 + 20 | 90 | 0 |
| compound (I-5) + methoxyfenozide (1:1) according to the invention | 100 + 100 | 80 | 0 |

*found = activity found
**calc. = activity calculated using Colby's formula

The invention claimed is:

1. A composition comprising (I-5), 4-{[(6-chloropyrid-3-yl)methyl](2,2-difluorethyl)amino}furan-2(5H)-one,

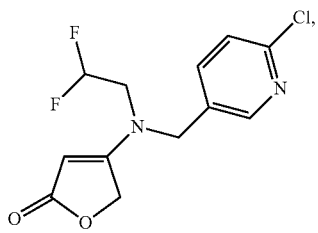

and methoxyfenozide

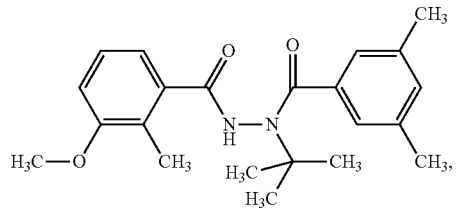

wherein the ratio of (I-5) to methoxyfenozide is from 5:1 to 1:5, and wherein (I-5) and methoxyfenozide are present in synergistic amounts.

2. A method for controlling insect pests, characterized in that the composition according to claim 1 is allowed to act on the insect pests.

3. A method for treating seed comprising treating seed with the composition according to claim 1.

4. A method for treating transgenic plants comprising treating transgenic plants with the composition according to claim 1.

5. A method for treating seed of transgenic plants comprising treating the seed of the transgenic plants with the composition according to claim 1.

6. A method for controlling insect pests, characterized in that (I-5), 4-{[(6-chloropyrid-3-yl)methyl](2,2-difluorethyl)amino}furan-2(5H)-one,

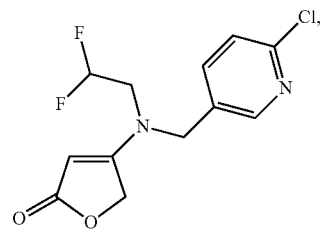 [SMILES: O=C1C=C(N(Cc2ccc(Cl)nc2)CC(F)F)CO1]

and methoxyfenozide

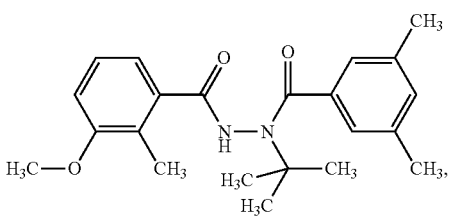

are allowed to act on the insect pests and/or their habitat and/or seed, wherein the ratio of (I-5) to methoxyfenozide is from 5:1 to 1:5, and wherein (I-5) and methoxyfenozide are present in synergistic amounts.

7. The method according to claim 6, wherein the seed is treated with I-5 and methoxyfenozide simultaneously.

8. The method according to claim 6, wherein the seed is treated with I-5 and methoxyfenozide at different times.

9. Seed treated with (I-5), 4-{[(6-chloropyrid-3-yl)methyl](2,2-difluorethyl)amino}furan-2(5H)-one,

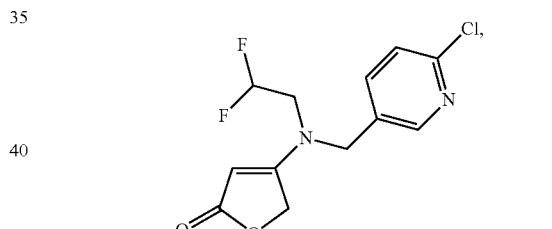

and methoxyfenozide

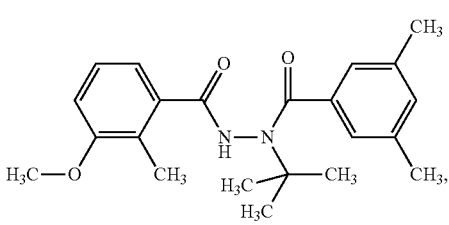

wherein the ratio of (I-5) to methoxyfenozide is from 5:1 to 1:5, and wherein (I-5) and methoxyfenozide are present in synergistic amounts.

10. The seed according to claim 9, characterized in that the seed is treated simultaneously with I-5 and methoxyfenozide.

11. The seed according to claim 9, characterized in that the seed is treated at different times with I-5 and methoxyfenozide.

* * * * *